United States Patent
Song et al.

(10) Patent No.: US 10,696,970 B2
(45) Date of Patent: Jun. 30, 2020

(54) PHARMACEUTICAL COMPOSITION FOR PREVENTING AND TREATING METABOLIC DISEASE COMPRISING MKRN1 EXPRESSION OR ACTIVITY INHIBITOR AS AN ACTIVE INGREDIENT

(71) Applicant: INDUSTRY-ACADEMIC COOPERATION FOUNDATION, YONSEI UNIVERSITY, Seoul (KR)

(72) Inventors: Jae Whan Song, Seoul (KR); Min Sik Lee, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/959,831

(22) Filed: Apr. 23, 2018

(65) Prior Publication Data

US 2018/0305698 A1    Oct. 25, 2018

(30) Foreign Application Priority Data

Apr. 21, 2017    (KR) ........................ 10-2017-0051624

(51) Int. Cl.

| C12N 15/113 | (2010.01) |
| A61P 1/16 | (2006.01) |
| A61P 3/06 | (2006.01) |
| A23L 33/13 | (2016.01) |
| A61P 3/10 | (2006.01) |
| A23L 33/17 | (2016.01) |

(52) U.S. Cl.
CPC .......... *C12N 15/1137* (2013.01); *A23L 33/13* (2016.08); *A23L 33/17* (2016.08); *A61P 1/16* (2018.01); *A61P 3/06* (2018.01); *A61P 3/10* (2018.01); *A23V 2002/00* (2013.01); *C12N 2310/14* (2013.01); *C12N 2320/30* (2013.01)

(58) Field of Classification Search
None
See application file for complete search history.

(56) References Cited

U.S. PATENT DOCUMENTS 9,284,329 B2    3/2016    Cravo et al.

FOREIGN PATENT DOCUMENTS

| JP | 4585186 B2 | 11/2010 |
| KR | 10-1504559 B1 | 3/2015 |
| KR | 10-1576793 A | 12/2015 |

OTHER PUBLICATIONS

Jin-Taek Hwang, et al., "Antiobesity Effect of Ginsenoside Rg3 involves the AMPK and PPAR-γ Signal Pathways", Phytotherapy Research, 2009, pp. 262-266, vol. 23.
J-H Kim, et al., "Suppression of PPAR γ through MKRN1-mediated ubiquitination and degradation prevents adipocyte differentiation", Cell Death and Differentiation, 2014, pp. 594-603, vol. 21.

*Primary Examiner* — Jennifer Pitrak McDonald
(74) *Attorney, Agent, or Firm* — Sughrue Mion, PLLC

(57) ABSTRACT

A pharmaceutical composition for preventing and treating metabolic diseases, which includes an MKRN1 expression or activity inhibitor as an active ingredient, is provided. Because the MKRN1 of the present invention functions as an E3 ligase, which ubiquitinates AMPKα, to degrade an AMPK protein, expression and activity levels of AMPK can be restored by suppressing the MKRN1 expression. Also, the MKRN1 expression or activity inhibitor of the present invention can be effectively used as an active ingredient of the composition for preventing and treating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets.

3 Claims, 52 Drawing Sheets
Specification includes a Sequence Listing.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: MKRN1 siRNA #6

<400> SEQUENCE: 1
cgggatcctc tccaactgca a                                              21

<210> SEQ ID NO 2
<211> LENGTH: 19
<212> TYPE: DNA
<213> ORGANISM: Artificial Sequence
<220> FEATURE:
<223> OTHER INFORMATION: MKRN1 siRNA #7

<400> SEQUENCE: 2
caggcgaagc tgagtcaag                                                 19
```

PHARMACEUTICAL COMPOSITION FOR PREVENTING AND TREATING METABOLIC DISEASE COMPRISING MKRN1 EXPRESSION OR ACTIVITY INHIBITOR AS AN ACTIVE INGREDIENT

CROSS-REFERENCE TO RELATED APPLICATION

This application claims priority to and the benefit of Korean Patent Application No. 2017-0051624, filed on Apr. 21, 2017, the disclosure of which is incorporated herein by reference in its entirety.

BACKGROUND

1. Field of the Invention

The present invention relates to a pharmaceutical composition and a health functional food for preventing and treating a metabolic disease, which include a Makorin ring finger protein-1 (MKRN1) expression or activity inhibitor as an active ingredient.

2. Discussion of Related Art

In modern society, obesity has emerged as one of the most menacing diseases in the $21^{st}$ century owing to the worldwide change to the western dietary lifestyles. A decrease in patients' life expectancy is induced by means of metabolic diseases caused by obesity such as diabetes, hypertension, hyperlipidemia, and the like. Approximately two-thirds of the population in the U.S. has been diagnosed with obesity, and more cases of obese patients are expected to appear in advanced countries. In recent years, it is estimated there are approximately 1.4 billion cases of obese patients around the world, and it was reported that 300 billion dollars per year is spent to treat obesity in the U.S.

As one of the metabolic diseases, diabetes is also a chronic disease of which the number of patients is gradually growing. By 2030, it is expected that there will be 440 million cases of diabetic patients around the world. Therefore, various drugs are currently being developed and sold in the market to treat obesity and diabetes. However, it has been reported that these drugs are gradually withdrawn from the market due to their side effects. As a pre-release phase, approximately 200 or more drugs have clinical or preclinical pipelines, but only a very small number of the drugs are sold in the market as they are reported to have side effects There are still few anti-obesity or antidiabetic drugs on the market, but the market for the drugs is gradually expanding. By 2021, it will be expected to expand to approximately 2.4 billion dollars in only the main advanced countries. In this way, there is an urgent need for succeeding in developing drugs, which have little side effects and that patients can take over a long period of time, as the anti-obesity or antidiabetic drugs.

AMPK is a main target protein for treating diabetes, which is known to be a very important factor that controls blood sugar and causes obesity and fatty liver, and has also been reported to have a correlation with metabolism-related cancers. Therefore, drugs have been developed to provide AMPK activity regulators or a target protein capable of regulating AMPK activity as therapeutic agents used to treat metabolic diseases.

For example, metformin which is an antidiabetic drug has a function as an AMPK activator, and may tend to alleviate metabolic diseases and significantly reduce cancer-related diseases when administered to patients. However, metformin has a drawback in that it cannot have an effect of completely curing diabetes. In recent years, the metabolic diseases have been treated using metoformin or derivatives thereof, but such a compound does not directly target AMPK capable of suppressing metabolism-related diseases, and there is no exact mechanism known for the mechanism of action of metoformin. Therefore, because metoformin is likely to cause side effects, there is a need for development of therapeutic agents used to treat metabolic diseases, which aim at targeting novel mechanisms and targets thereof.

Accordingly, the present inventors have endeavored to find novel target proteins capable of targeting the promotion of AMPK activity, and found that since an MKRN1 protein functions as an E3 ligase, which ubiquitinates AMPKα, to degrade an AMPK protein, expression and activity levels of AMPK can be restored in cells in which the MKRN1 expression is suppressed. Also, the present inventors have found that an MKRN1 expression or activity inhibitor can be effectively used as an active ingredient of the composition for preventing and treating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets. Therefore, the present invention has been completed based on these facts.

PRIOR-ART DOCUMENT

Patent Document

Patent Document 1: KR 10-1504559 B1

SUMMARY OF THE INVENTION

Accordingly, the present inventors have found that an improving effect on obesity, diabetes and fatty liver can be exhibited following MKRN1 expression inhibition in an obese mouse model group in which the MRKN1 expression and activity are suppressed. Therefore, the present invention has been completed based on these facts.

The present invention is directed to a pharmaceutical composition for preventing and treating metabolic diseases.

Also, the present invention is directed to a health functional food for preventing and alleviating metabolic diseases.

According to an aspect of the present invention, there is provided a pharmaceutical composition for preventing and treating metabolic diseases, which includes an MKRN1 expression or activity inhibitor as an active ingredient.

According to another aspect of the present invention, there is provided a health functional food for preventing and alleviating metabolic diseases, which includes an MKRN1 expression or activity inhibitor as an active ingredient.

According to still another aspect of the present invention, there is provided a method of preventing or treating metabolic diseases, which includes administering an effective amount of the MKRN1 expression or activity inhibitor to a subject suffering from a metabolic disease.

According to one preferred embodiment of the present invention, the MKRN1 expression or activity inhibitor may include one or more selected from the group consisting of an antisense nucleotide, siRNA, and shRNA, all of which complementarily bind to mRNA of a gene encoding MKRN1.

According to another preferred embodiment of the present invention, the MKRN1 expression or activity inhibitor may enhance the expression and activity of 5'-AMP-activated protein kinase (AMPK).

According to still another preferred embodiment of the present invention, the metabolic diseases may be selected from the group consisting of obesity, type 2 diabetes, dyslipidemia, insulin resistance, hepatic steatosis, and non-alcoholic fatty liver.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 2A shows that AMPK is phosphorylated in cells in which the MKRN1 expression is suppressed, and FIGS. 2B to 2E show the mutual binding of an AMPK protein to an MKRN1 protein;

FIG. 3A shows an expression level of an AMPK domain in cells in which MKRN1 is knocked down, FIG. 3B shows a change in expression level of the AMPK domain depending on the concentration of MKRN1 expressed, and FIG. 3C shows that a change in the degree of degradation of the AMPK protein by MKRN1 is confirmed when cells are treated with MG132 which is a proteasome inhibitor;

FIG. 4A shows confirmation of the presence of ubiquitin for an AMPKα subunit confirmed when MKRN1 is or is not expressed, FIGS. 4B and 4C shows the results of confirming that MKRN1 is an E3 ligase for the AMPKα protein at an in vitro level, and FIG. 4D shows a decrease in ubiquitination of AMPKα when MKRN1 is suppressed in an environment in which cells are treated with MG132 which is a proteasome inhibitor;

FIG. 6A shows relative proportions of DEGs in MKRN1-null liver and adipose tissues according to their associated GOBPs: The GOBP terms at level 1 (left) and levels 2 to 4 (right) were used for general cellular processes and metabolic processes, respectively, FIG. 6B shows cellular processes related to lipid and carbohydrate metabolism enriched by the up- and down-regulated genes identified in MKRN1-null liver or adipose tissue: The bars represent −log 10 (p-value), where the p-value is the significance of the processes being enriched by the up- or down-regulated genes, FIG. 6C shows Heat maps showing the changes in the expression of DEGs involved in fatty acid biosynthesis and β-oxidation, gluconeogenesis and thermogenesis: The color bar shows the gradient of the $\log_2$-fold-changes of mRNA expression levels in MKRN1-depleted samples relative to those in WT samples, and FIGS. 6D and 6E show network models describing alterations of metabolic reactions regulated by DEGs in MKRN1-null livers (D) and adipose tissue (E): Arrows denote metabolic reactions, and dotted lines denote the transportation of molecules or regulation involving intermediate regulators between the linked molecules. Node colors represent up-(red) or down-regulation (green) in MKRN1-null livers or adipose tissue. The color bar represents the gradient of the $\log_2$-fold-changes of mRNA expression levels induced by MKRN1 ablation relative to those in WT;

FIG. 9A is a diagram for comparing obese mice in which obesity is induced by high-fat diets when MKRN1 is or is not suppressed, FIG. 9B shows changes in body weights in an obese mouse model when MKRN1 is or is not suppressed, FIG. 9C shows daily feed uptake in the obese mouse model when MKRN1 is or is not suppressed, and FIG. 9D shows a difference in blood concentration of leptin in an obese mouse model when MKRN1 is or is not suppressed;

FIG. 10A shows the results of confirming, through micro CT imaging, that adipose tissues are formed in the obese mouse model when MKRN1 is or is not suppressed, FIG. 10B shows changes in weights and areas of the adipose tissues in the obese mouse model when MKRN1 is or is not suppressed, FIG. 10C shows the adipose tissues in the obese mouse model and the results of hematoxylin and eosin staining (H&E staining) of the adipose tissues when MKRN1 is or is not suppressed, FIG. 10D shows the results of observing brown adipose tissues in an obese mouse model when MKRN1 is or is not suppressed, FIG. 10E shows expression and phosphorylation levels of an AMPK protein in the adipose tissues in the obese mouse model when MKRN1 is or is not suppressed, and FIG. 10F shows blood triglyceride, total cholesterol and LDL cholesterol concentrations in the obese mouse models when MKRN1 is or is not suppressed;

FIG. 11A shows a difference in blood sugar (plasma insulin) in a diabetic mouse model when MKRN1 is or is not suppressed, and FIG. 11B shows GTT confirmation in the diabetic mouse model when MKRN1 is or is not suppressed;

FIG. 12A shows a comparison of sizes and weights of livers in a fatty liver mouse model when MKRN1 is or is not suppressed, FIG. 12B shows a comparison of deposition of fats in hepatocytes in a fatty liver mouse model when MKRN1 is or is not suppressed, FIG. 12C shows a comparison of concentrations of neutral fats in hepatocytes in the fatty liver mouse model when MKRN1 is or is not suppressed, FIG. 12D shows a difference in expression and phosphorylation levels of AMPK in the fatty liver mouse model when MKRN1 is or is not suppressed, and FIGS. 12E and 12F shows the results of AST and ALT analyses for hepatic function tests in the fatty liver mouse model when MKRN1 is or is not suppressed;

FIG. 14A shows that male B6 mice (6 weeks old) are fed an HFD for 9 weeks and then injected with either PBS or adenoviruses expressing GFP via the tail vein (Ad_control, Ad_shMK1#1 and #2 (shRNA targeting MKRN1): After 1 week of continuous HFD feeding, the mice are sacrificed and analyzed, FIG. 14B shows immunoblot analysis of GFP expression in extracts from the indicated tissues (Sub, subcutaneous fat; Epi, epididymal fat) of mice infected with an adenovirus (n=2), FIGS. 14C and 14D show that Liver (C) and BAT (D) lysates from adenovirus-injected mice are analyzed by immunoblotting as indicated, FIG. 14E shows body weights of HFD-fed male mice measured every 2 days for 8 days (n=5 mice per group), FIG. 14F shows representative H&E staining of liver sections, FIG. 14G shows that liver TG levels are measured, FIG. 14H shows that lipogenic enzymes are analyzed via quantitative real-time PCR (n=5 mice per group), FIG. 14I shows representative H&E staining of epididymal fat (top) and subcutaneous fat (bottom) sections, FIG. 14J shows the weights of fat tissues recorded following sacrifice, and FIG. 14K shows liver TG levels (n=5 mice per group): Plasma lipid (TG, cholesterol, and FFA) concentrations in 24-h-fasted mice (n=5 mice per group): The data is expressed as the mean±S.D., and two-tailed Student's t-test; $*P \leq 0.05$, $**P \leq 0.01$.

DETAILED DESCRIPTION OF EXEMPLARY EMBODIMENTS

Figure 1:
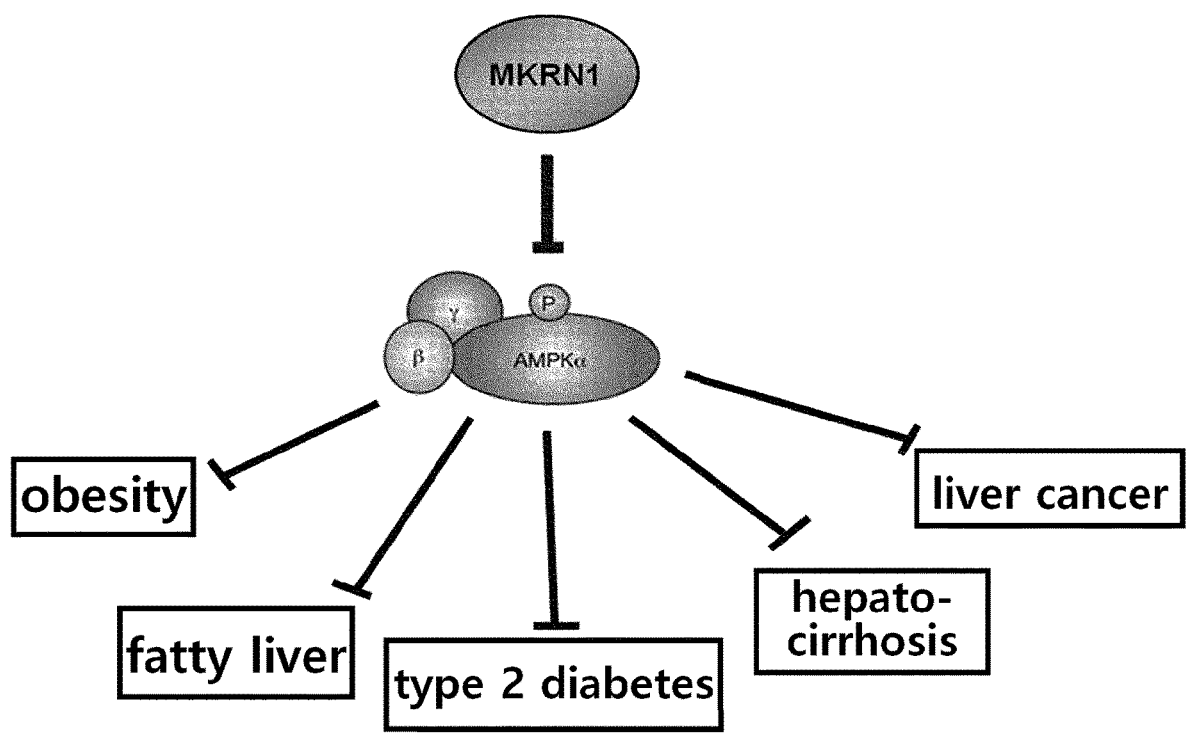
FIG. 1 is a schematic diagram showing the flow in which an improving effect on type 2 diabetes, fatty liver and obesity can be induced because the activity of AMPK can be induced when MKRN1 is suppressed.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclature used in this specification and the experimental methods described below are widely known and generally used in the related art.

As described above, although there is an increasing demand for effective therapeutic agents for diabetes and obesity, research on novel targets and therapeutic agents for metabolic diseases is continuously conducted because drugs whose related mechanisms and targets have not been completely identified do not have a therapeutic effect and may also have a probability of causing side effects. However, no effective therapeutic agents are reported yet.

Because the MKRN1 of the present invention functions as an E3 ligase, which ubiquitinates AMPKα, to degrade an AMPK protein, expression and activity levels of AMPK can be restored by suppressing the MKRN1 expression. Also, the MKRN1 expression or activity inhibitor of the present invention can be effectively used as an active ingredient of the composition for preventing and treating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets.

Therefore, the present invention provides a pharmaceutical composition for preventing and treating metabolic diseases, which includes an MKRN1 expression or activity inhibitor as an active ingredient.

The "MKRN1 expression or activity inhibitor" of the present invention preferably includes one or more selected from the group consisting of an antisense nucleotide, siRNA and shRNA, all of which complementarily bind to mRNA of a gene encoding MKRN1, but the present invention is not limited thereto.

The siRNA is preferably a nucleotide having a base sequence set forth in SEQ ID NO: 1 or 2, but the present invention is not limited thereto. For example, any type of siRNA may be used as long as it is prepared by a method known in the related art as a method of preparing siRNA, such as chemical synthesis, amplification of a desired nucleotide sequence by a polymerase chain reaction (PCR), or purification of preexisting siRNA through recombinant synthesis.

The "MKRN1 expression or activity inhibitor" of the present invention preferably enhances the expression and activity of AMPK, but the present invention is not limited thereto. For example, the enhancement of the AMPK activity may be more preferably understood to mean an increase in a phosphorylation level of AMPK.

The "metabolic diseases" of the present invention are preferably selected from the group consisting of obesity, type 2 diabetes, dyslipidemia, insulin resistance, hepatic steatosis, and non-alcoholic fatty liver. Specifically, the metabolic diseases are more preferably obesity, type 2 diabetes, or hepatic steatosis, but the present invention is not limited thereto.

Figure 2A:
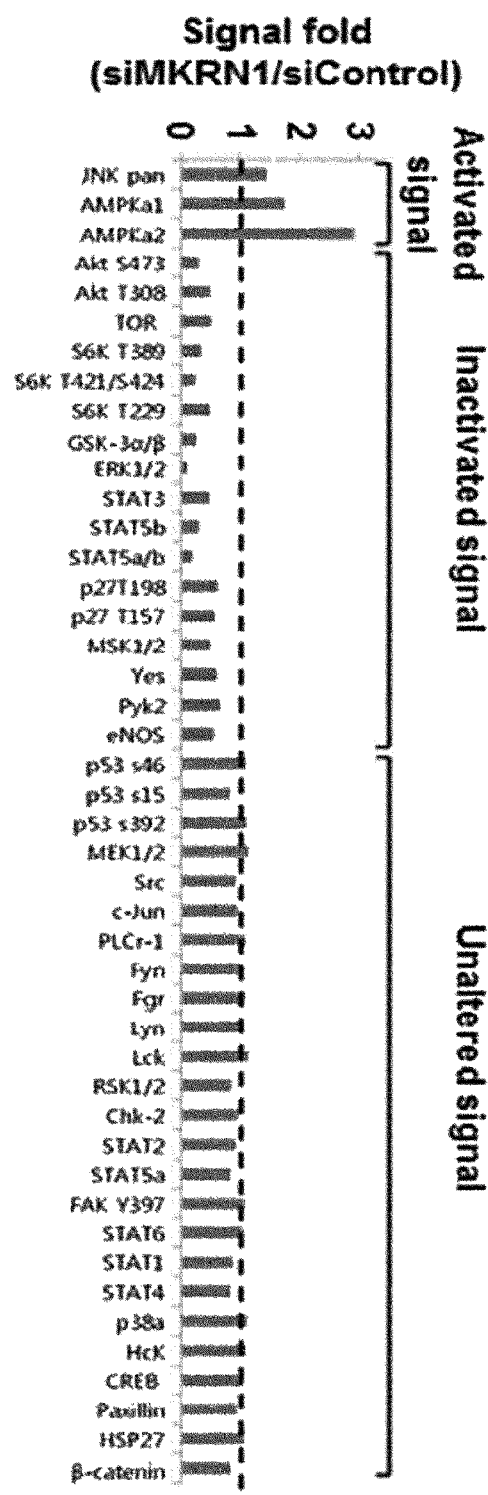
FIGS. 2A through 2E are diagrams for confirming the binding of an AMPK α subunit to MKRN1.
Figure 2B:
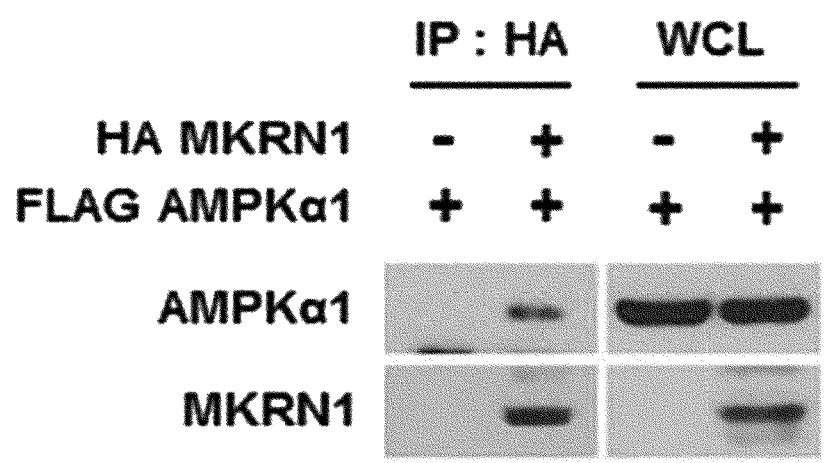
Figure 2C:
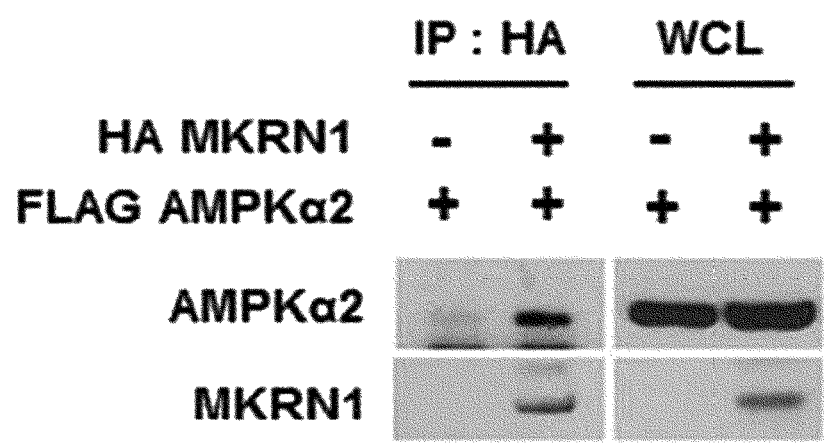
Figure 2D:
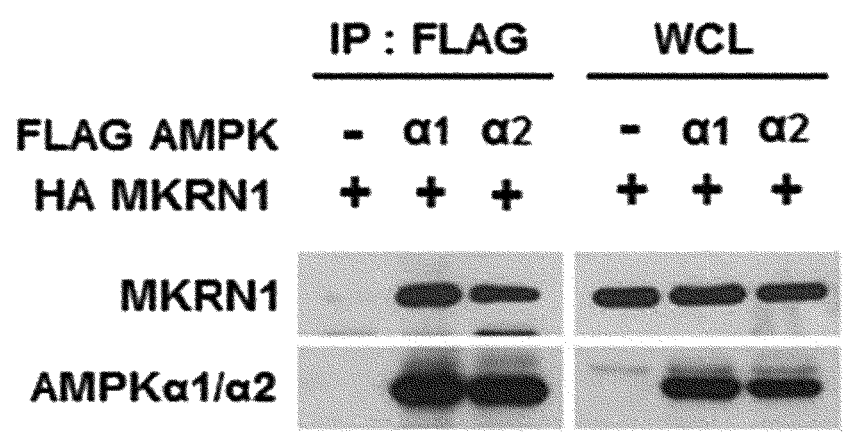
Figure 2E:
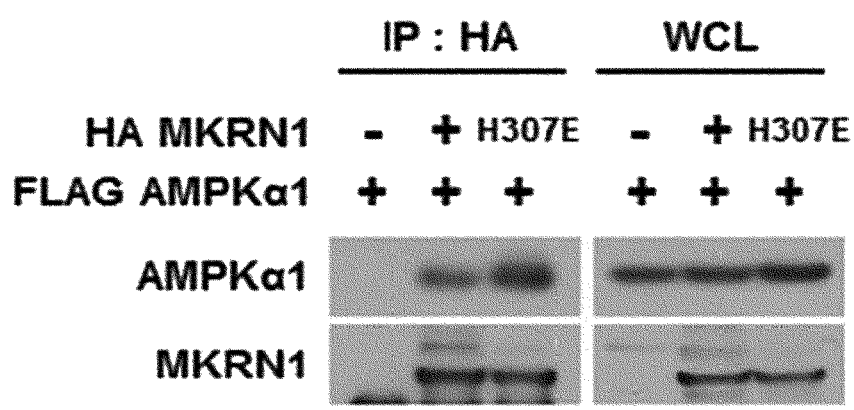
Figure 3A:
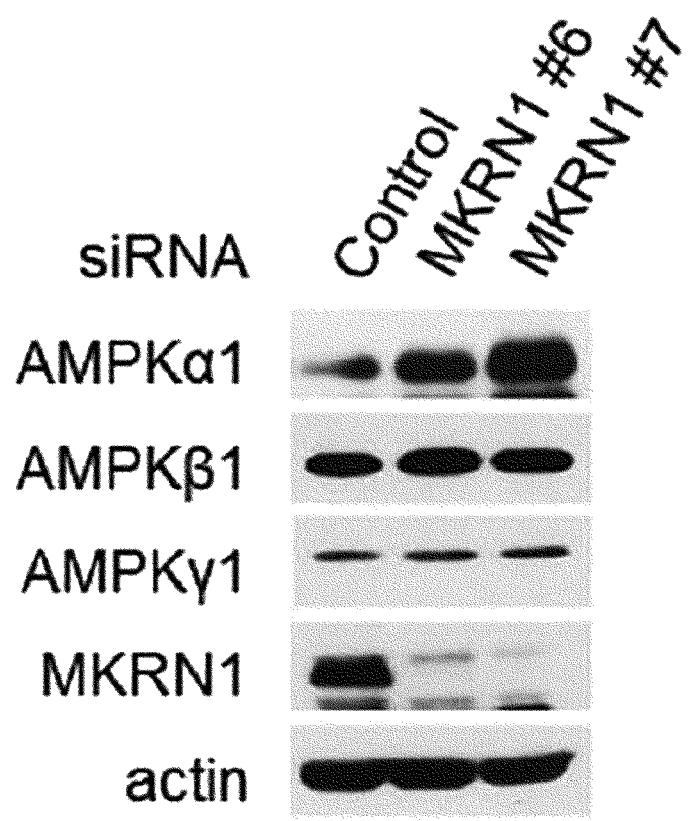
FIGS. 3A through 3C are diagrams for identifying the role of MKRN1 as a factor for degrading and suppressing an AMPK protein.

According to specific embodiments of the present invention, the present inventors have checked a process of regulating AMPK degradation by MKRN1, and found that MKRN1 is present in a state in which AMPK is mutually bound to the MKRN1 in cells (FIG. 2), and that MKRN1 degrades AMPK so that the AMPK can be regulated so as not to be activated (FIG. 3A). It was confirmed that such degradation is induced through a proteasome when MKRN1 functions as an E3 ligase, which ubiquitinates AMPK, so that MKRN1 specifically binds to an AMPKα protein (FIGS. 3 and 4). Therefore, it was confirmed that, because the MKRN1 regulates AMPK to reduce expression and phosphorylation levels of AMPK, the subsequent related AMPK signaling pathway and glycolysis are regulated so as to be suppressed (FIG. 5).

Also, the present inventors have designed obese, diabetic and fatty liver mouse models through high-fat diets in order to check an effect of MKRN1 on metabolic diseases because MKRN1 inhibits the expression and activity of AMPK. An MKRN1$^{+/+}$ (WT) mouse group and an MKRN1$^{-/-}$ (KO) mouse group were bred for 16 weeks, and an improving effect on obesity, diabetes and fatty liver through the MKRN1 suppression was investigated. As a result, it was confirmed that although there is no significant difference in diet in the mouse group in which MKRN1 is knocked out, a body weight, fat mass, and blood triglyceride and cholesterol levels were reduced to exhibit an obesity improvement effect (FIG. 10). Also, it was confirmed that hyperinsulinemia may be significantly alleviated in the mouse group in which MKRN1 is knocked out to exhibit a diabetes alleviating effect (FIG. 11). In addition, it was confirmed that a size and weight of hepatic tissues are reduced and the fat deposition is slowed down in the mouse group in which MKRN1 is knocked out, and effects of reducing the fat deposition in the hepatocytes and improving the hepatic function are exhibited (FIGS. 12 and 13).

Therefore, because the MKRN1 of the present invention functions as an E3 ligase, which ubiquitinates AMPKα, to degrade an AMPK protein, expression and activity levels of AMPK can be restored by suppressing the MKRN1 expression. Also, the MKRN1 expression or activity inhibitor of the present invention can be effectively used as an active ingredient of the composition for preventing and treating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets.

The siRNA of the present invention includes a separate sense RNA strand homologous with the target sequence and an antisense RNA strand complementary to the sense RNA strand, or may be a single RNA strand having a stem-loop structure in which the sense RNA strand and the antisense RNA strand are connected by loops.

The siRNA is not limited to a complete pairing of a double-stranded RNA region having a RNA pair, and may have a hairpin structure with a stem-loop structure, which is particularly referred to as a short hairpin RNA (shRNA). Meanwhile, the double-stranded or stem region may also include an unpaired region in which pairs are not formed due to mismatching (the corresponding bases are not complementary to each other), bulging (there are no bases corresponding to a unidirectional chain), and the like. The total length of the region is in a range of 10 to 80 bases, preferably in a range of 15 to 60 bases, and more preferably in a range of 20 to 40 bases. Also, the loop region has no particular meaning in terms of a sequence thereof, but simply has approximately 3 to 10 bases to connect an antisense sequence to a sense sequence at a proper distance, and may be used without limitation.

A siRNA terminal structure may have both a blunt terminal structure and a cohesive terminal structure. The cohesive terminal structure may have both a 3'-terminal protruding structure and a 5'-terminal protruding structure, and the number of protruding bases thereof is not limited. For example, the number of the bases may be in a range of 1 to 8 bases, preferably in a range of 2 to 6 bases. Also, siRNA may include low-molecular-weight RNAs (for example, natural or artificial RNA molecules such as tRNA, rRNA, viral RNA, and the like) in a range that can maintain an effect of suppressing the expression of a target gene, for example, at a protruding region of one terminus. The siRNA terminal structure does not need to have truncated structures at both sides thereof, and may also have a stem-loop structure in which a terminal region of one side of double-stranded RNA is connected via linker RNA. A length of the linker is not particularly limited as long as it does not interfere with base pairing in a stem region.

A composition of the present invention may include various oral or parenteral formulations. When formulated, the composition may be prepared using one or more buffers (for example, saline or PBS), antioxidants, bacteriostatic agents, chelating agents (for example, EDTA or glutathione), fillers, extending agents, binders, adjuvants (for example, aluminum hydroxide), suspending agents, thickening agents, wetting agents, disintegrating agents or surfactants, diluents or excipients.

Also, a solid preparation for oral administration includes a tablet, a pill, a powder, a granule, a capsule, and the like. Such a solid preparation is prepared by mixing one or more excipients, for example, starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethyl cellulose and hydroxypropylmethyl cellulose or gelatin, with one or more compounds. For example, a tablet or a sugar-coated tablet may be obtained by blending the active ingredient with a solid excipient, grinding the resulting mixture, adding a suitable adjuvant thereto, and processing the mixture into a granular mixture.

Lubricants such as magnesium stearate, talc and the like are also used in addition to the simple excipients. A liquid preparation for oral administration includes a suspending agent, a preparation for internal use, an emulsion or a syrup. In this case, the liquid preparation for oral administration may include various excipients, for example, a wetting agent, a sweetening agent, a flavoring agent, a preservative, and the like in addition to the generally used simple diluents such as water or liquid paraffin. Also, cross-linked polyvinyl pyrrolidone, agar, alginic acid or sodium alginate, and the like may be added as a disintegrating agent, when necessary. Further, the pharmaceutical composition may further include an anti-agglomerating agent, a lubricant, a wetting agent, a fragrance, an emulsifying agent, a preservative, and the like.

A preparation for parenteral administration includes a sterile aqueous solution, a non-aqueous solvent, a suspension, an emulsion, a freeze-dried preparation, or a suppository. Propylene glycol, polyethylene glycol, a vegetable oil such as olive oil, or an injectable ester such as ethyl oleate may be used as the non-aqueous solvent or the suspension. Witepsol, Macrogol, Tween 61, cacao butter, laurin butter, glycerol, gelatin, and the like may be used as a base of the suppository.

The composition of the present invention may be orally or parenterally administered. The composition may be formulated into various forms such as a solution for external use on the skin upon parenteral administration; an injectable solution which is administered by intraperitoneal, intraectal, intravenous, intramuscular, subcutaneous, endometrial or intracerebroventricular injection; a preparation for percutaneous administration; or a nasal inhalant according to methods known in the related art.

The injectable solution must be sterilized, and protected from being contaminated by microbes such as bacteria and fungi. In the case of the injectable solution, examples of the suitable carrier may include a solvent or a dispersion medium such as water, ethanol, polyols (for example, glycerol, propylene glycol, liquid polyethylene glycol, and the like), a mixture thereof and/or vegetable oil, but the present invention is not limited thereto. More preferably, Hanks' solution, Ringer's solution, triethanolamine-containing phosphate-buffered saline (PBS) or sterile water for injections, or an isotonic solution such as 10% ethanol, 40% propylene glycol, and 5% dextrose may be used as the suitable carrier. The injectable solution may further include various antimicrobial and antifungal agents such as paraben, chlorobutanol, phenol, sorbic acid, thimerosal, and the like so as to protect the injectable solution from being contaminated by microbes. In most cases, the injectable solution may also further include an isotonic agent such as sugar or sodium chloride.

The composition of the present invention is administered in a pharmaceutically effective amount. In the present invention, the term "pharmaceutically effective amount" refers to an amount sufficient to treat a disease at a reasonable benefit/risk ratio applicable to any medical treatment. In this case, a level of the effective dose may be determined depending on the type of a patient's disease, severity, the activity of a drug, the sensitivity to the drug, an administration time, a route of administration, and a secretion rate, a therapeutic period, factors including drugs to be used together, and other factors well known in the field of medicine. The composition of the present invention may be administered as an individual therapeutic agent, or may be administered in combination with other therapeutic agents. In this case, the composition may be administered sequentially or concurrently with conventional therapeutic agents, and may be administered in a single dose or multiple doses. That is, the total effective amount of the composition of the present invention may be administered to patients in a single dose, and may be administered according to a fractionated treatment protocol in which multiple doses are administered for a long period of time. By considering all the aforementioned factors, it is important to administer the composition at a dose in which the maximum effect can be achieved without any side effects when administered at a minimum dose. Thus, the dose of the composition may be easily determined by those skilled in the related art.

A dose of the pharmaceutical composition according to the present invention may vary depending on the weight, age, sex, health condition, and diet of a patient, an administration time, a mode of administration, a secretion rate, and the severity of a disease.

For parenteral administration, the composition of the present invention may be administered once or several times a day so that the daily dose is preferably in a range of 0.01 to 50 mg, more preferably 0.1 to 30 mg, based on 1 kg of body weight based on a cereal extract. For oral administration, the composition of the present invention may be administered once or several times a day so that the daily dose of the composition is preferably in a range of 0.01 to 100 mg, more preferably 0.01 to 10 mg, based on 1 kg of body weight. However, because the daily dose of the composition may increase or decrease depending on a mode of administration, the severity of obesity, the sex, weight and age of a patient, etc., the dose is not intended to limit the scope of the present invention in any fashion.

The composition of the present invention may be used alone or in conjunction with surgery, radiotherapy, hormone therapy, chemotherapy, and methods using a biological response modifier.

Also, the present invention provides a health functional food for preventing and alleviating metabolic diseases, which includes an MKRN1 expression or activity inhibitor as an active ingredient.

The "MKRN1 expression or activity inhibitor" of the present invention preferably includes one or more selected from the group consisting of an antisense nucleotide, siRNA, and shRNA, all of which complementarily bind to mRNA of a gene encoding MKRN1, but the present invention is not limited thereto.

The siRNA is preferably a nucleotide having a base sequence set forth in SEQ ID NO: 1 or 2, but the present invention is not limited thereto. For example, any type of siRNA may be used as long as it is prepared by a method known in the related art as a method of preparing siRNA, such as chemical synthesis, amplification of a desired nucleotide sequence by a polymerase chain reaction (PCR), or purification of preexisting siRNA through recombinant synthesis.

The "MKRN1 expression or activity inhibitor" of the present invention preferably enhances the expression and activity of AMPK, but the present invention is not limited thereto. For example, the enhancement of the AMPK activity may be more preferably understood to mean an increase in a phosphorylation level of AMPK.

The "metabolic diseases" of the present invention are preferably selected from the group consisting of obesity, type 2 diabetes, dyslipidemia, insulin resistance, hepatic steatosis, and non-alcoholic fatty liver. Specifically, the metabolic diseases are more preferably obesity, type 2 diabetes, or hepatic steatosis, but the present invention is not limited thereto.

Because the MKRN1 of the present invention functions as an E3 ligase, which ubiquitinates AMPKα, to degrade an AMPK protein, expression and activity levels of AMPK can be restored by suppressing the MKRN1 expression. Also, the MKRN1 expression or activity inhibitor of the present invention can be effectively used as an active ingredient of the health functional food for preventing and alleviating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets.

A food composition according to the present invention may be prepared into various forms according to conventional methods known in the related art. Common foods may be prepared by adding the composition of the present invention to beverages (including alcoholic beverages), fruits and processed foods thereof (e.g., canned fruits, bottling, jam, marmalade, and the like), fish, meat and processed foods thereof (e.g., ham, sausage, corn beef, and the like), bread and noodles (e.g., udon, buckwheat noodles, ramen, spaghetti, macaroni, and the like), fruit juices, various drinks, cookies, taffy, dairy products (e.g., butter, cheese, and the like), edible vegetable oils, margarine, vegetable proteins, retort foods, frozen foods, various condiments (e.g., soybean paste, soy sauce, sauce, and the like), and the like, but the present invention is not limited thereto. Also, the nutritional supplement may be prepared by adding the composition of the present invention to capsules, tablets, pills, and the like, but the present invention is not limited thereto. In addition, the health functional food may be, for example, prepared into liquids, granules, capsules and powders so that the composition of the present invention itself can be prepared into the form of teas, juices and drinks to ingest health drinks, but the present invention is not limited thereto. To use the composition of the present invention in the form of food additives, the composition of the present invention may also be prepared into the form of powders or concentrates, and used. Further, the health functional food may be prepared into the form of compositions by being mixed with active ingredients known to have an effect of preventing and alleviating metabolic diseases.

When the composition of the present invention is used as a health drink, the health drink composition may further contain additional components such as various flavoring agents or natural carbohydrates as in conventional drinks. The aforementioned natural carbohydrates may include monosaccharides such as glucose, fructose, and the like; disaccharides such as maltose, sucrose, and the like; polysaccharides such as dextrin, cyclodextrin, and the like; and sugar alcohols such as xylitol, sorbitol, erythritol, and the like. Natural sweetening agents such as thaumatin, a *stevia* extract, and the like; synthetic sweetening agents such as saccharin, aspartame, and the like may be used as the sweetening agent. A ratio of the natural carbohydrate is generally in a range of approximately 0.01 to 0.04 g, preferably approximately 0.02 to 0.03 g per 100 mL of the composition of the present invention.

Also, the composition of the present invention may be included as the active ingredient of the food composition for preventing and alleviating metabolic diseases. In this case, an amount of the composition of the present invention refers to an amount effective for achieving the effect of preventing and alleviating metabolic diseases, but the present invention is not particularly limited thereto. For example, the amount is preferably in a range of 0.01 to 100% by weight, based on the total weight of the composition. The food composition of the present invention may be prepared by mixing the composition with other active ingredients known to be effective for preventing and alleviating metabolic diseases.

In addition to the aforementioned components, the health food of the present invention may contain various nutrients, vitamins, electrolytes, a flavoring agent, a coloring agent, pectic acid, pectates, alginic acid, alginates, organic acids, a protective colloidal thickening agent, a pH control agent, a stabilizing agent, a preservative, glycerin, an alcohol, or a carbonating agent. In addition, the health food of the present invention may include pulp for preparing a natural fruit juice, a fruit juice drink or a vegetable drink. Such components may be used alone or in combination. The ratio of such additives is not important, but the additives are generally chosen in a range of 0.01 to 0.1 part by weight, based on 100 parts by weight of the composition of the present invention.

Further, the present invention provides a method of preventing or treating metabolic diseases, which includes administering an effective amount of an MKRN1 expression or activity inhibitor to a subject suffering from a metabolic disease.

The "MKRN1 expression or activity inhibitor" is as described above, and thus a repeated description thereof is omitted for clarity.

Hereinafter, the present invention will be described in further detail with reference to examples thereof. However, it will be apparent to those skilled in the art that the following examples are merely given herein to describe the present invention more fully, but are not intended to limit the scope of the present invention.

Example 1

Confirmation of Process of Regulating AMPK Degradation by MKRN1

<1-1> Confirmation of Mutual Binding of MKRN1 and AMPK

To check an effect of the MKRN1 of the present invention on the activity of AMPK, first of all, the relationship between MKRN1 and AMPK was verified.

Specifically, HeLa cells were transformed with MKRN1 siRNA (Qiagen-Xeragon Inc., CA) to suppress the expression of MKRN1 in order to prepare cells in which MKRN1 was inhibited, and the cells were then cultured. After the culturing, the cells were recovered, and compared to the MKRN1-expressing normal control (siControl) using a phospho-kinase assay kit (R&D Systems, ARY003). Then, a group of proteins whose phosphorylation levels were significantly increased was screened.

As a result, it was confirmed that the phosphorylation level of AMPK increased in the MKRN1-inhibited cells, as shown in FIG. 2A. From these results, it was confirmed that AMPK was activated when MKRN1 was inhibited (FIG. 2A).

Also, because it was confirmed that the AMPK was activated through the inhibition of MKRN1, the binding between MKRN1 and AMPK was verified in order to check whether the activation of such AMPK was induced by the binding with MKRN1.

Specifically, a 293T cancer cell line was transformed with a HA-MKRN1 vector for the expression of HA-tagged MKRN1 and/or a FLAG-AMPK vector for the expression of FLAG-tagged AMPK, and then cultured. After the culturing, the cells were recovered, and homogenized to obtain a whole cell extract (WCL).

Thereafter, the whole cell extract (WCL) was immunoprecipitated using an anti-HA antibody or an anti-FLAG antibody. Then, immunoblotting was performed using the whole cell extract or the immunoprecipitated extract as a sample. For the immunoblotting, an anti-AMPKα1 antibody, an anti-AMPKα2 antibody or an anti-MKRN1 antibody was used as the primary antibody, and an anti-mouse IgG antibody was used as the secondary antibody. The same experiment was performed using a H307E variant of MKRN1 as the negative control to check the results depending on the activity of MKRN1.

As a result, as shown in FIGS. 2B to 2E, it was confirmed through the immunoprecipitation that MKRN1 was present in the cytoplasm in a state in which the MKRN1 was bound to an AMPK protein in the cells in which the MKRN1 was overexpressed (FIGS. 2B to 2E).

<1-2> Confirmation of Promotion of AMPK Degradation by MKRN1

Because the MKRN1 was present in a state in which the MKRN1 was bound to AMPK in the cells and the AMPK was activated in the MKRN1-inhibited cells, it was confirmed whether the MKRN1 degraded the AMPK so that the AMPK was not activated.

Specifically, HeLa cells were transformed with MKRN1 siRNA #6 (SEQ ID NO: 1: 5'-CGGGATCCTCTCCAACT-GCAA-3') or #7 (SEQ ID NO: 2: 5'-CAGGCGAAGCT-GAGTCAAG-3') to suppress the MKRN1 expression in order to prepare cells in which MKRN1 was inhibited, and the MKRN1-inhibited cells were cultured. After the culturing, the cells were recovered, and homogenized to obtain a whole cell extract (WCL). Thereafter, the whole cell extract (WCL) was subjected to immunoblotting. For the immunoblotting, an anti-AMPKα1 antibody, an anti-AMPKβ1 antibody, an anti-AMPKγ1 antibody, or an anti-MKRN1 antibody was used as the primary antibody, and an anti-mouse IgG antibody was used as the secondary antibody. Actin was selected as the control to compare the expression of the protein in the cell extract. HeLa cells which were not transformed with siRNA were used as the normal control.

As a result, as shown in FIG. 3A, it was confirmed that an expression level of an AMPKα subunit significantly increased in the cells in which the MKRN1 expression was knocked down using siRNA, compared to the normal control (FIG. 3A).

<1-3> Confirmation of Role of MKRN1 as AMPK Protein-Degrading and Inhibiting Factor More specifically, the role of MKRN1 when MKRN1 degraded AMPK was verified. Particularly, in a proteasome complex which rapidly degraded essential proteins generated by mutations or post-transcriptional damages, it was checked whether the MKRN1 functioned as an E3 ligase ubiquitinating a substrate to be degraded by MKRN1.

Specifically, a HeLa cell line was transformed with a varying concentration of the HA-MKRN1 vector used in Example <1-2>, further transformed with an AMPKα1-FLAG vector, an AMPKα2-FLAG vector, an AMPKβ1-FLAG vector, or an AMPKγ1-FLAG vector, and then cultured. After the culturing, each of the cells were recovered, and homogenized to obtain a whole cell extract (WCL). Thereafter, the whole cell extract (WCL) was subjected to immunoprecipitation using an anti-FLAG antibody. Then, immunoblotting was performed using the whole cell extract or the immunoprecipitated extract as a sample. For the immunoblotting, an anti-AMPKα1 antibody, an anti-AMPKα2 antibody, an anti-AMPKβ1 antibody, an anti-AMPKγ1 antibody, or an anti-MKRN1 antibody was used as the primary antibody, and an anti-mouse IgG antibody was used as the secondary antibody. GFP was selected as the control to compare the expression of the protein in the cell extract.

Figure 3B:
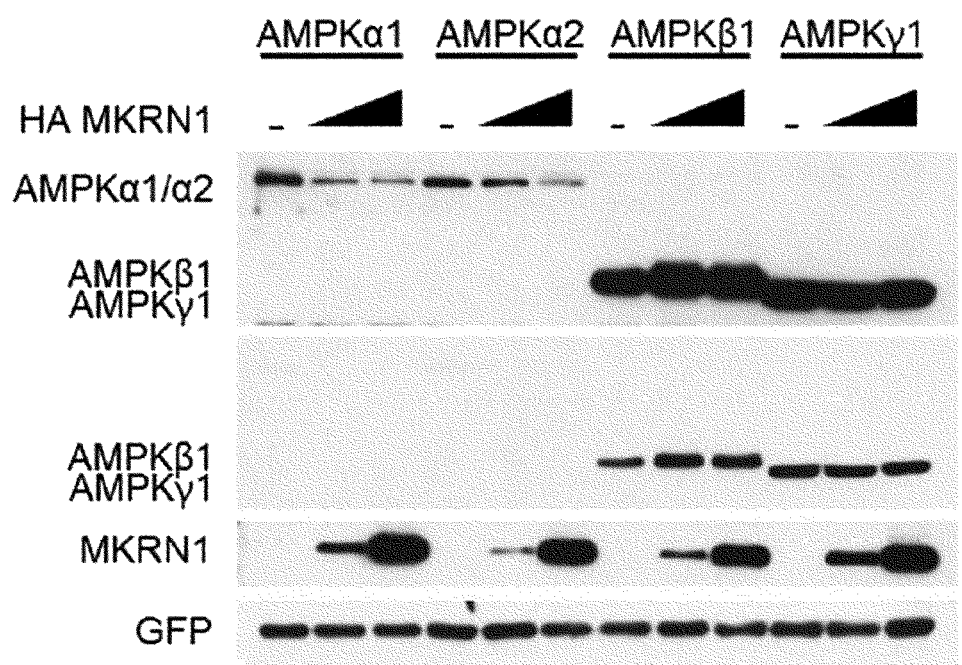

As a result, it was confirmed that the MKRN1 protein expressed in a concentration-dependent fashion in the cell line significantly suppressed an expression level of an a domain among three domains of AMPK, as shown in FIG. 3B. From these results, it was confirmed that the MKRN1 of the present invention was the E3 ligase for the AMPKα protein (FIG. 3B).

Also, to check whether the degradation of the AMPKα protein by MKRN1 occurred by a typical protein degradation process through the proteasome in the cells, it was checked whether the AMPKα protein was degraded by MKRN1 under an environment in which the cells were treated with a proteasome inhibitor MG132.

Specifically, HeLa cells were transformed with a HA-MKRN1 vector and/or an AMPKα1-FLAG vector or an AMPKα2-FLAG vector, and the transformed cells were cultured for 4 hours in a culture medium containing 10 μg/mL of MG132. After the culturing, the cells were recovered, and homogenized to obtain a whole cell extract (WCL). Then, the whole cell extract (WCL) was subjected to immunoblotting. For the immunoblotting, an anti-AMPKα1 antibody, an anti-AMPKα2 antibody, or an anti-MKRN1 antibody was used as the primary antibody, and an anti-mouse IgG antibody was used as the secondary antibody.

Figure 3C:
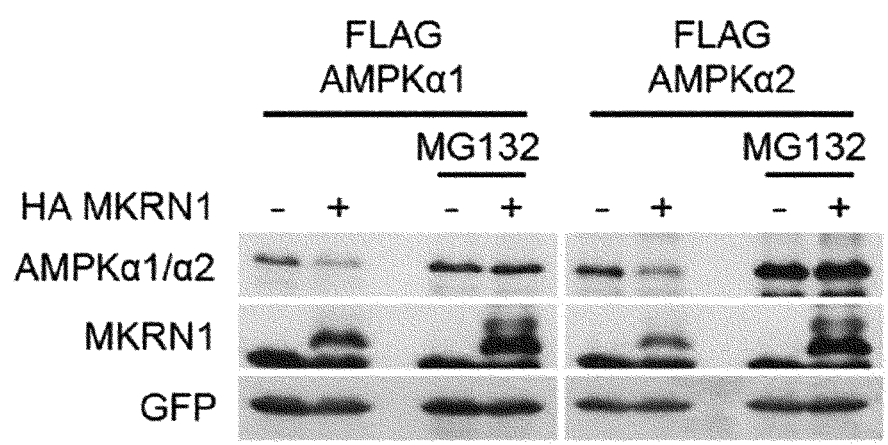

As a result, it was confirmed that the degradation of the AMPKα protein by MKRN1 was blocked by MG132, as shown in FIG. 3C. From these results, it was confirmed that the MKRN1 specifically bound to the AMPKα protein to induce the protein degradation through the proteasome (FIG. 3C).

<1-4> Confirmation of Role of MKRN1 as E3 Ligase Inducing Ubiquitination of AMPK It was expected that MKRN1 could degrade the AMPKα protein through a "poly-ubiquitination"/"proteasome" mechanism by verifying the proteasomic degradation of the AMPKα protein by MKRN1. Also, it was confirmed that the degradation of the AMPKα protein through the poly-ubiquitination could be induced by MKRN1.

Specifically, HeLa cells were transformed with an MKRN1 expression vector, a FLAG-AMPK vector and/or a HA-Ub vector used to express HA-tagged ubiquitin (Ub), and the transformed cells were cultured for 4 hours in a culture medium containing 10 μg/mL of MG132. After the culturing, the cells were recovered, and homogenized to obtain a whole cell extract. Thereafter, the whole cell extract was subjected to immunoprecipitation using an anti-FLAG antibody. Then, immunoblotting was performed using the immunoprecipitated extract as a sample. For the immunoblotting, an anti-HA antibody was used as the primary antibody, and an anti-mouse IgG antibody conjugated to horseradish peroxidase was used as the secondary antibody. Also, the whole cell extract (WCL) was subjected to immunoblotting to check the expression of an AMPK domain in the cells as well.

Figure 4A:
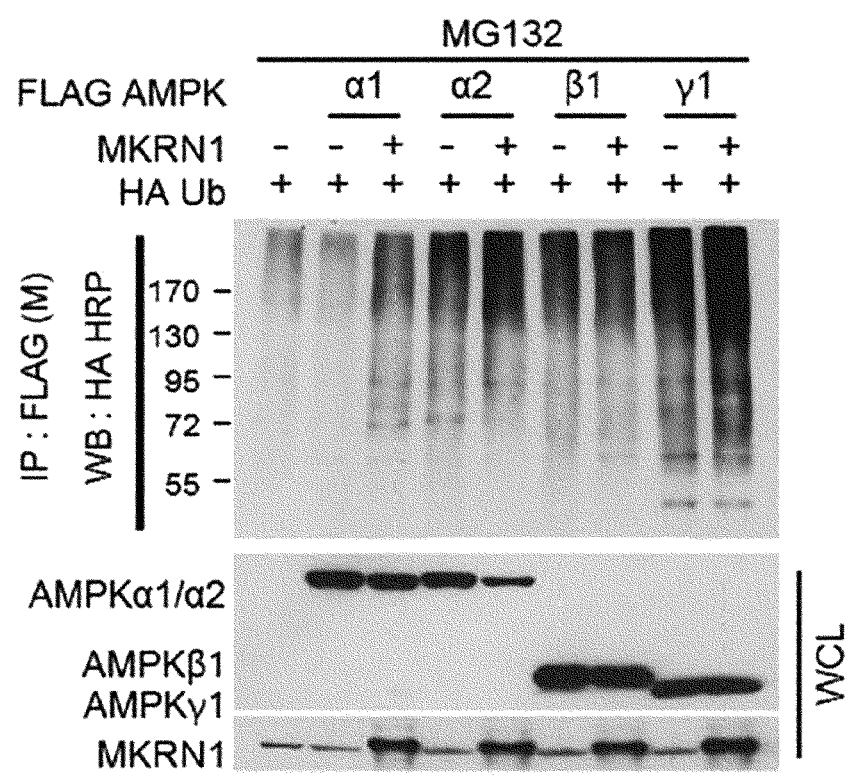
FIGS. 4A through 4D are diagrams for confirming the poly-ubiquitination of AMPK by MKRN1.
Figure 5:
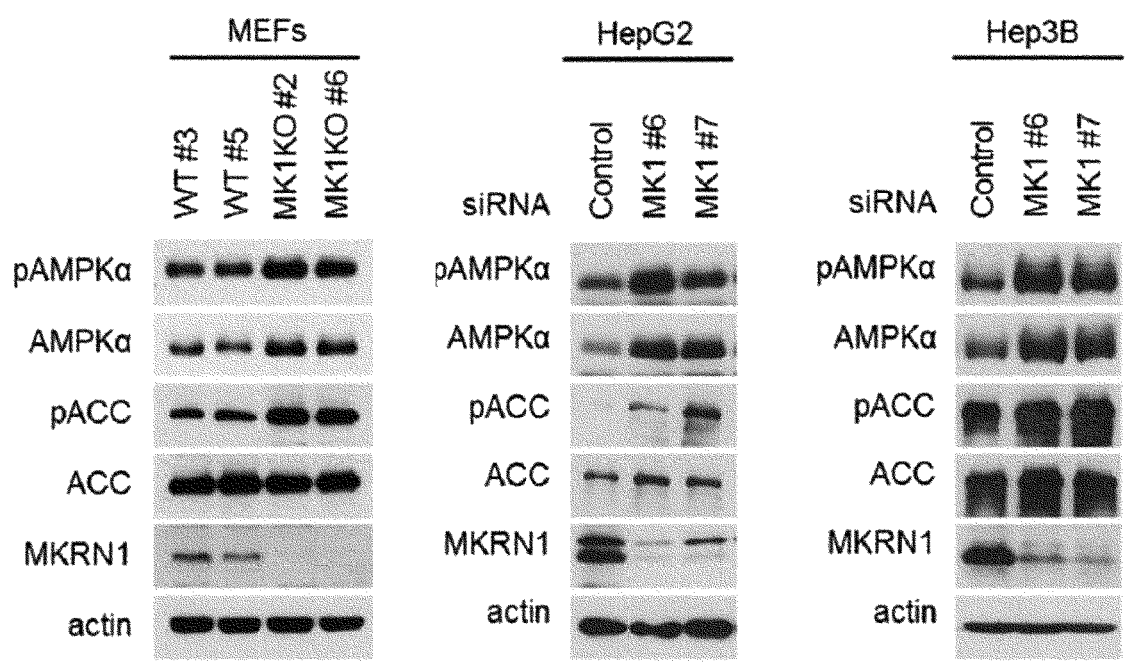
FIG. 5 is a diagram for confirming that an AMPK signaling pathway is suppressed by MKRN1: which shows a restoration of expression and activity levels of the AMPK protein by the MKRN1 knockout or knockdown.

As a result, it was confirmed that more ubiquitination specific to the AMPKα protein occurred in the cells in which all of the MKRN1, Hb and AMPK were expressed, compared to the cells in which MKRN1 was not expressed, as shown in FIG. 4A. From these results, it was confirmed that the MKRN1 functioned as a ubiquitin ligase for the AMPKα subunit (FIG. 4A).

Also, it was confirmed that the MKRN1 was the E3 ligase ubiquitinating the AMPK, indicating that this was once more verified at an in vitro level.

Specifically, Escherichia coli was transformed with an expression vector expressing GST-MKRN1 (WT) or a H307E variant of GST-MKRN1 and/or a vector expressing GST-AMPKα1, and the cells were then cultured. After the culturing, the cells were recovered, and homogenized to obtain a whole cell extract. Then, a GST-fused protein was separated using glutathione-sepharose. The separated protein was added to 20 μL of a reaction buffer (40 mM Tris, 50 mM NaCl, 5 mM MgCl$_2$, 2 mM ATP, 1 mM dithiothreitol, pH 7.6) together with 250 ng of E2 (UbcH5c, E2-627, Boston Biochem) and 5 μg of ubiquitin (U-100H, Boston Biochem) to induce a reaction at 37° C. for 3 hours. When the reaction was completed, the resulting reaction solution was subjected to immunoblotting using a protein solution. For the immunoblotting, an anti-AMPKα1 antibody or an anti-AMPKα2 antibody was used as the primary antibody, and an anti-mouse IgG antibody conjugated to horseradish peroxidase was used as the secondary antibody.

Figure 4B:
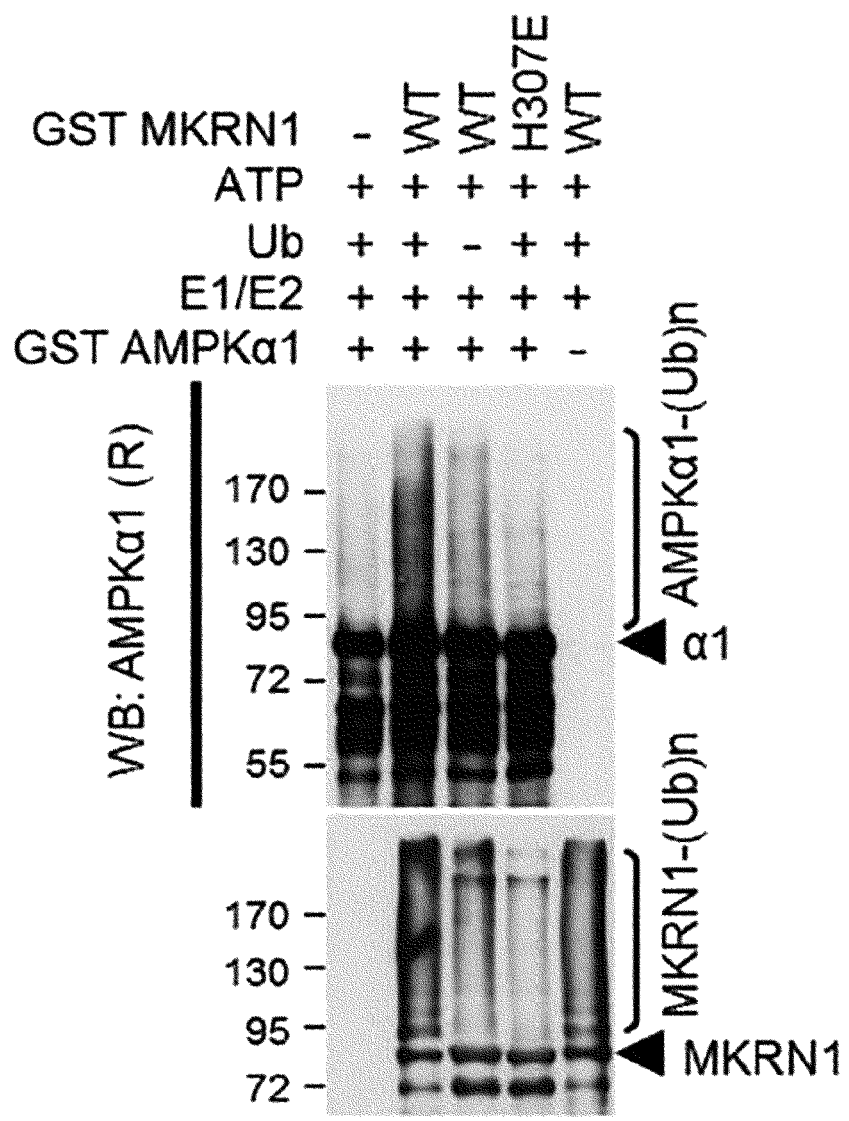
Figure 4C:
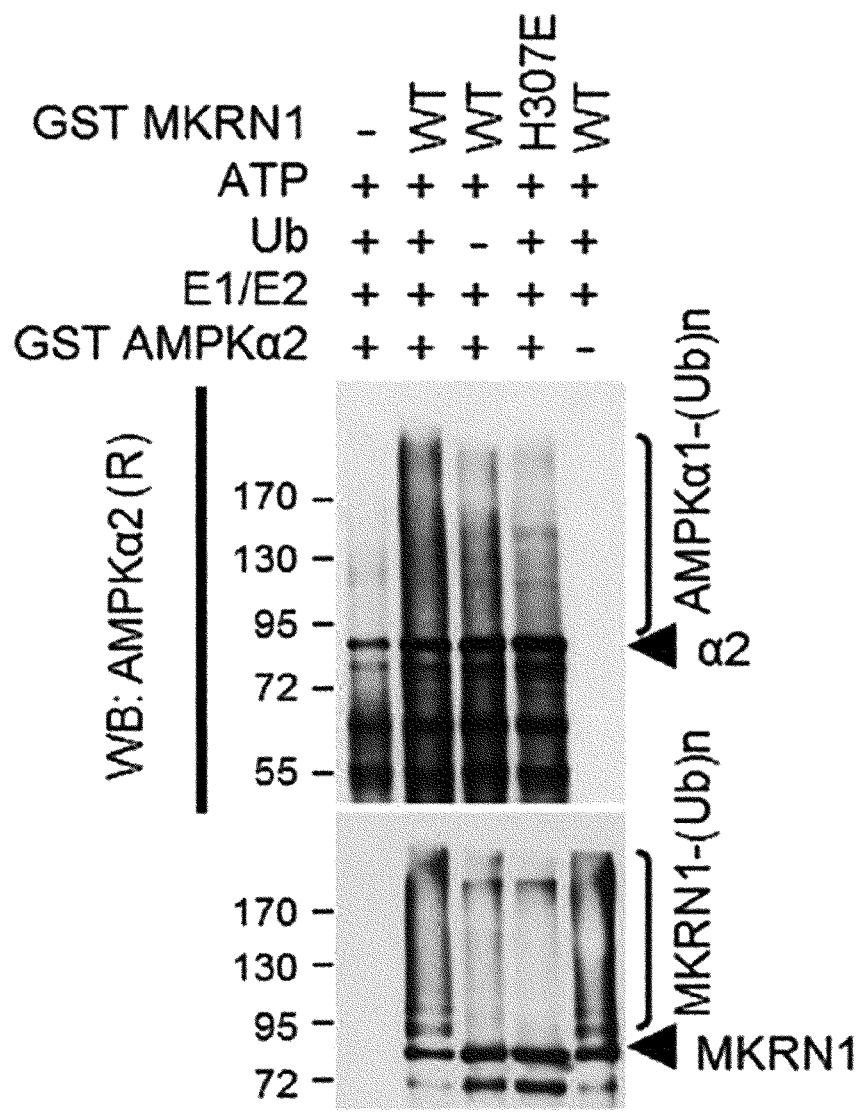

As a result, as shown in FIGS. 4B and 4C, it was confirmed that MKRN1 functioned as the E3 ligase for the AMPKα protein (FIGS. 4B and 4C).

Further, it was confirmed to what extent the MKRN1 contributed to the ubiquitination of the endogenous AMPK protein in the cells.

Specifically, the cells prepared in Example <1-1> in which the MKRN1 was inhibited by siRNA were seeded in a culture medium containing 10 μg/mL of MG132, and then cultured for 4 hours. After the culturing, the cells were recovered, and homogenized to obtain a whole cell extract. Then, the whole cell extract was subjected to immunoblotting. For the immunoblotting, an anti-Ub antibody was used as the primary antibody, and an anti-mouse IgG antibody conjugated to horseradish peroxidase was used as the secondary antibody. Also, the whole cell extract (WCL) was subjected to immunoblotting to check the expression of the AMPK domain in the cells as well.

Figure 4D:
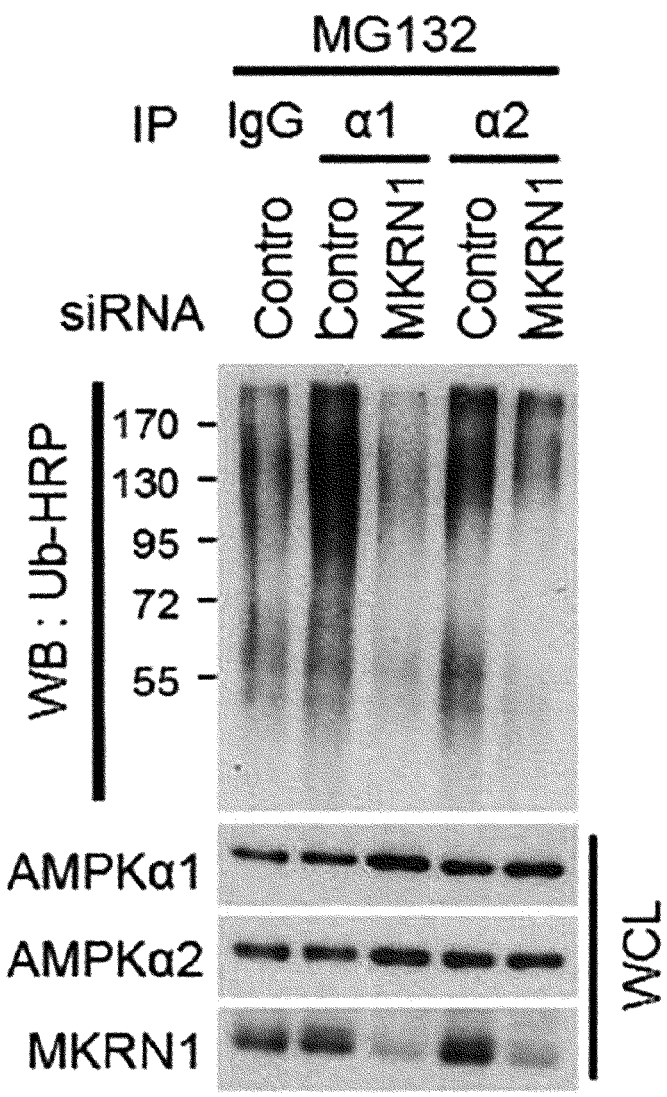

As a result, it was confirmed that the poly-ubiquitination of AMPK hardly occurred in the absence of MKRN1, as shown in FIG. 4D. From these results, it was confirmed that the MKRN1 functioned as a potent E3 ligase for the AMPKα subunit (FIG. 4D).

<1-5> Confirmation of Role of MKRN1 as Inhibitor Against AMPK Signaling

To check an effect of MKRN1 on AMPK signaling, an expression level and activity of the AMPK protein in an MKRN1-knockout mouse-derived cell line and an MKRN1-knockdown cell line were verified.

Specifically, a mouse embryonic fibroblast (MEF) cell line and a HepG2 or Hep3B cell line were transformed with MKRN1 siRNA #6 or #7 to suppress the MKRN1 expression in order to prepare cells in which MKRN1 was inhibited, and the MKRN1-inhibited cells were cultured. After the culturing, the cells were recovered, and homogenized to obtain a whole cell extract (WCL). Then, the whole cell extract (WCL) was subjected to immunoblotting. For the immunoblotting, an anti-AMPKα antibody, an anti-pAMPKα antibody, an anti-ACC antibody, an anti-pACC antibody, or an anti-MKRN1 antibody was used as the primary antibody, and an anti-mouse IgG antibody was used as the secondary antibody. Actin was selected as the control to compare the expression of the protein in the cell extract. MEF, HepG2 or Hep3B cells which were not transformed with siRNA were used as the normal control.

As a result, it was confirmed that an expression level of the AMPK protein significantly increased when the MKRN1 expression was suppressed through the knockout or knockdown, as shown in FIG. 5. From these results, it was confirmed that a level of phosphorylated AMPK (phospho-AMPK) increased as well (FIG. 5). Also, it was confirmed that the expression and phosphorylation levels of acetyl-CoA carboxylase (ACC), which is a downstream molecule of the signaling pathway regulated by the AMPK, increased. From these results, it was confirmed that the activation of the AMPK signaling pathway in the cells was possible only through the suppression of MKRN1 (FIG. 5).

Example 2

Confirmation of Metabolic Regulation by MKRN1 and AMPK

<2-1> Confirmation of Regulatory Effect on Lipid Metabolism According to Suppression of MKRN1 Expression Many existing reports showed that the carbohydrate and lipid metabolisms are regulated by activating an AMPK signaling pathway in cells, thereby regulating energy metabolism in the cells. Specifically, it is known that the consumption and degradation of carbohydrates and lipids are promoted by phosphorylating various downstream molecules of pathways through the activation of the AMPK signaling pathway, and thus the deposition of glycogen or fats from the carbohydrates and lipids in the cells is suppressed.

Figure 6A:
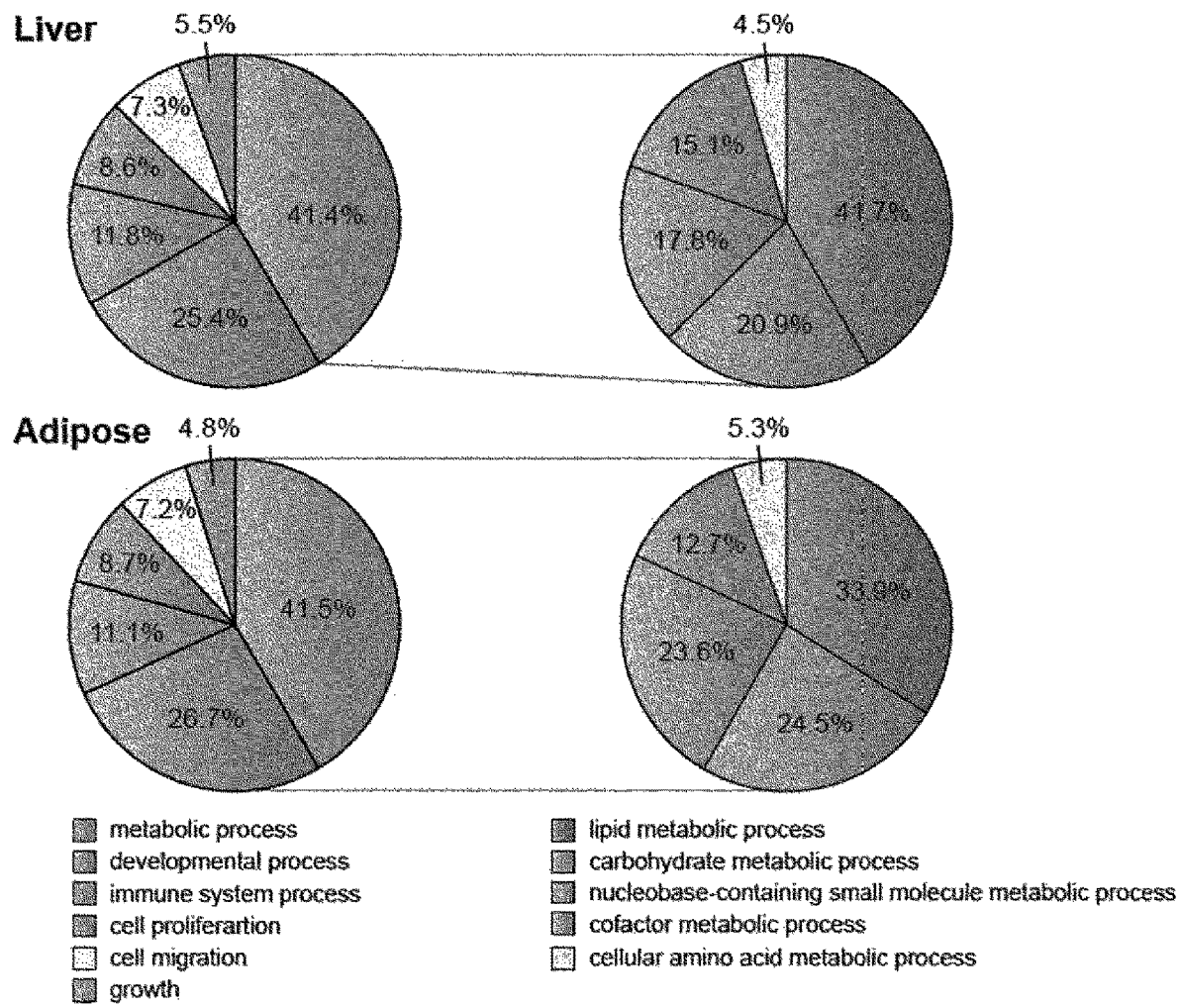
FIGS. 6A through 6E show the regulation of lipid and glucose metabolism by MKRN1 and AMPK.
Figure 6B:
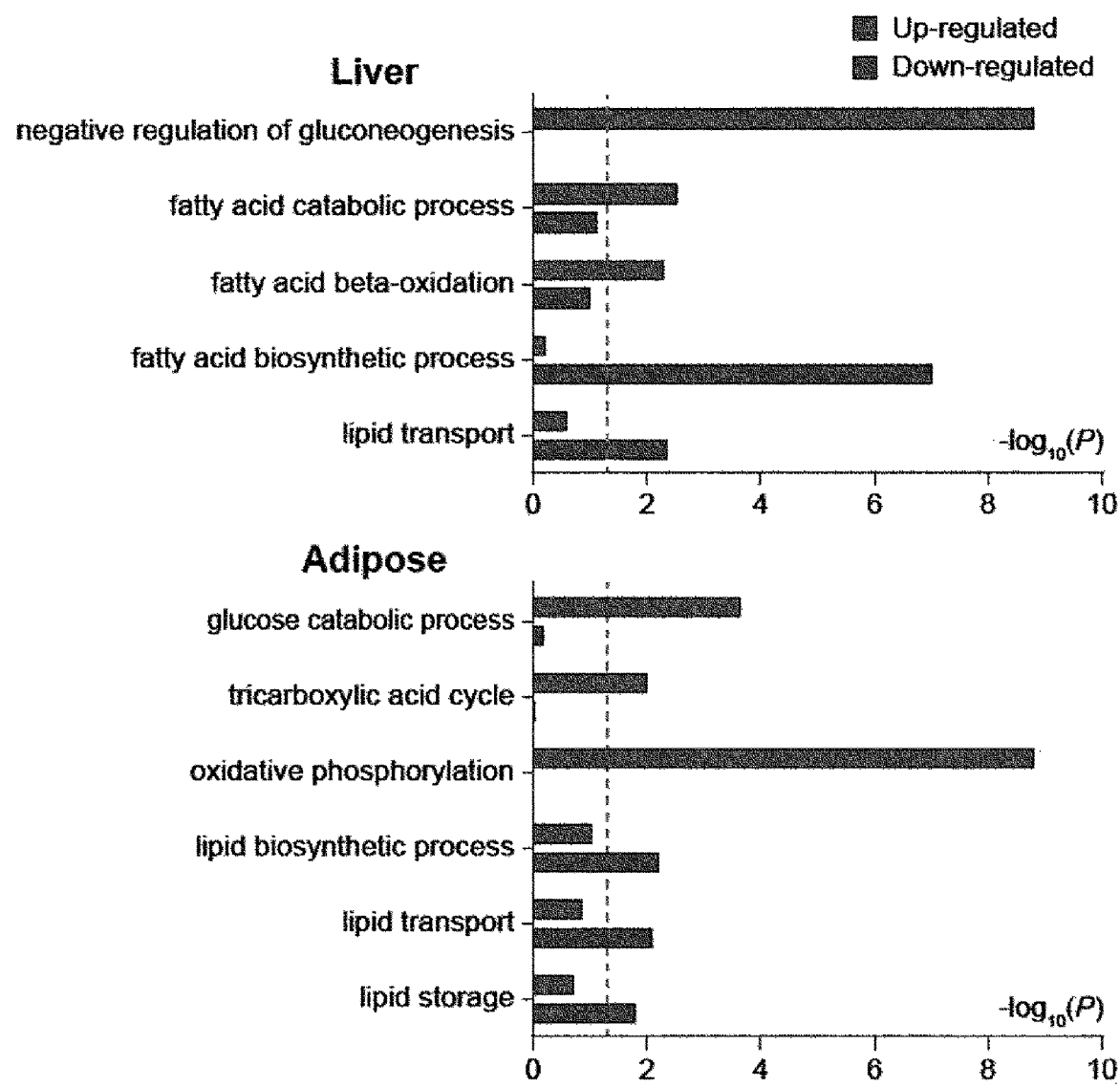
Figure 6C:
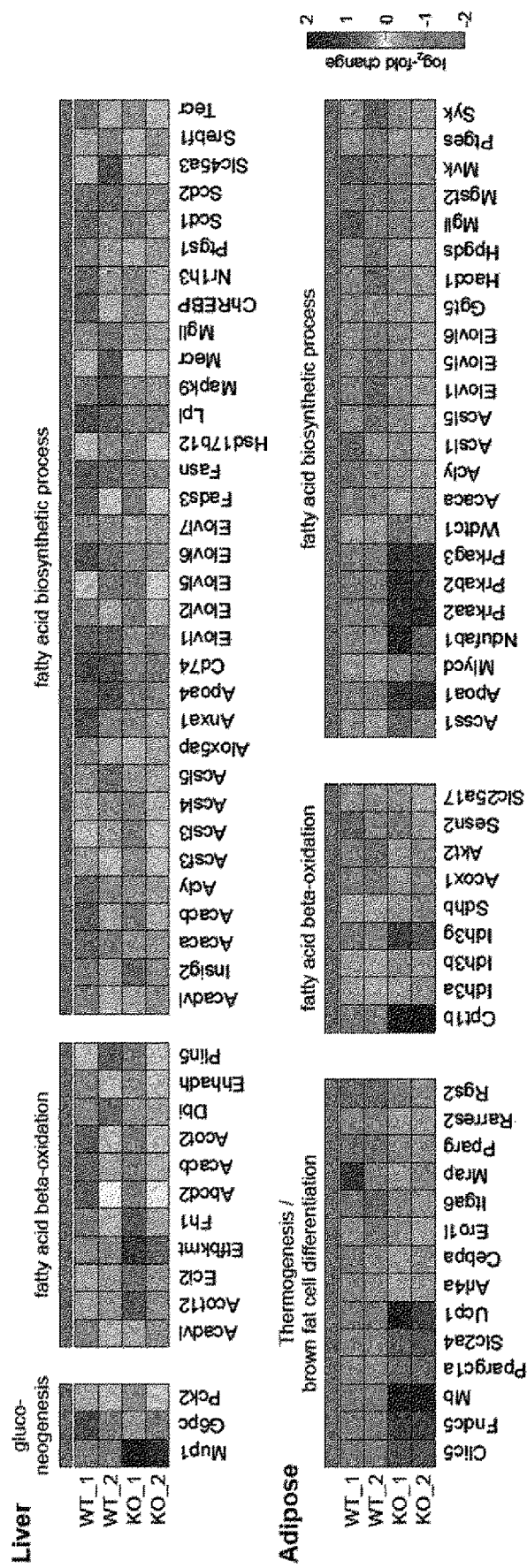
Figure 6D:
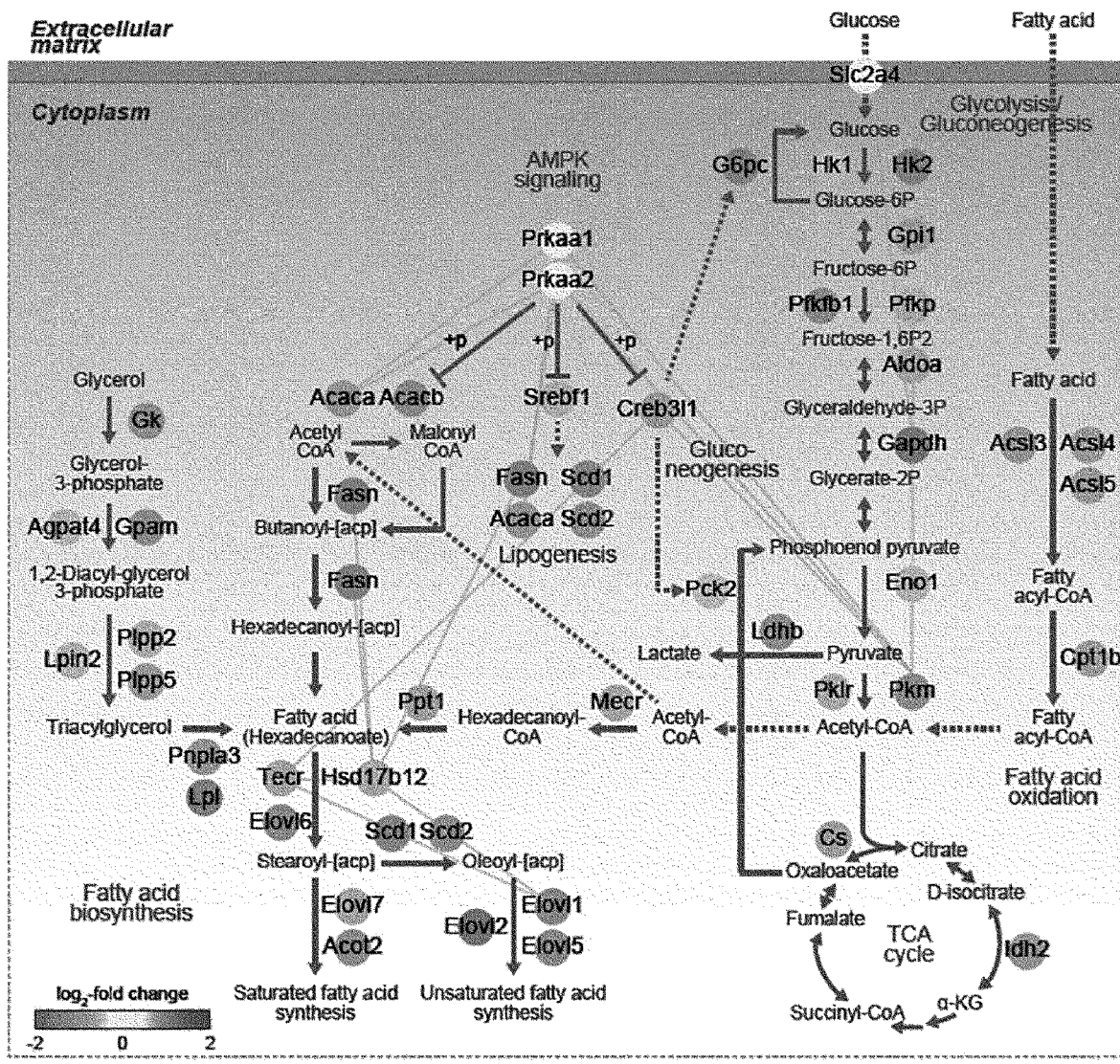
Figure 6E:
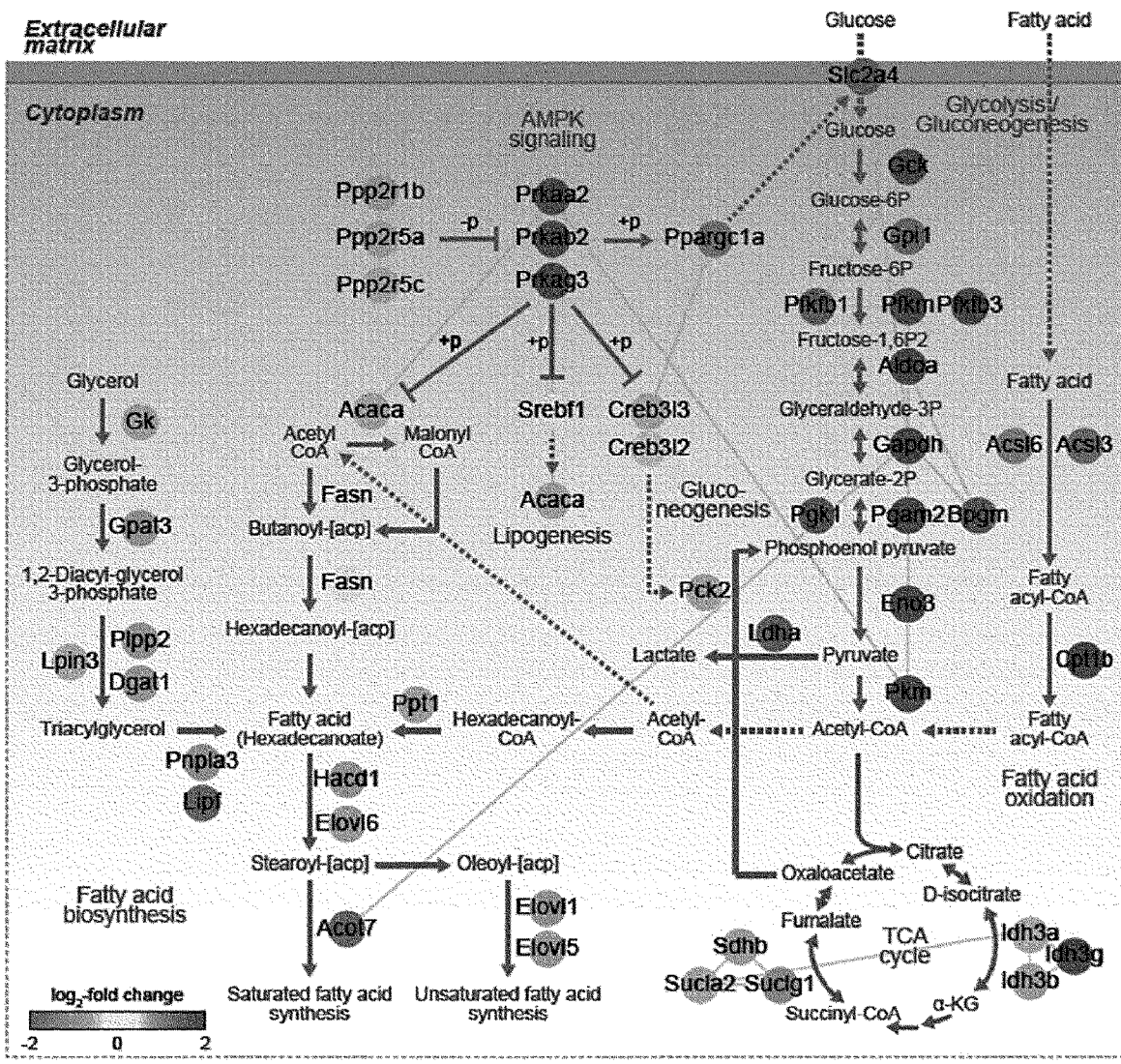

To examine how metabolic processes are affected by MKRN1 ablation, further functional enrichment analyses of the DEGs in the liver and adipose tissue were carried out. Among different functional categories, the DEGs were found to be most strongly associated (41.4% in the liver and 41.5% in adipose tissue) with metabolism, suggesting that MKRN1 depletion significantly impacts metabolic processes in the liver and adipose tissue (FIG. 6A, left). Notably, lipid metabolism (41.7% in the liver and 33.9% in adipose tissue) was one of the processes that was most influenced by MKRN1 ablation, together with carbohydrate metabolism (20.9% in the liver and 24.5% in adipose tissue) (FIG. 6A, right). Among cellular processes related to lipid metabolism, lipid anabolism pathways (i.e., lipid and fatty acid biosynthetic processes) were significantly (P<0.05) down-regulated in both MKRN1-null liver and adipose tissues (FIGS. 6B to 6E). In the liver, the genes involved in the biosynthesis of saturated and unsaturated fatty acids from acetyl-CoA (Acaca/b, Fasn, Tecr, Hsd17b12, Elovl1/2/5/6/7, Scd1/2 and Acot2) were down-regulated, as were the genes involved in the conversion of glycerol to fatty acids (Gk, Agpat4, Gpam, Lpin2, Plpp2/5, Pnpla3 and Lpl), suggesting systematic suppression of fatty acid biosynthetic pathways by MKRN1 ablation (FIG. 6D). In adipose tissue, similar down-regulation of fatty acid biosynthetic pathways was observed (FIG. 6E). On the other hand, the genes involved in lipolysis (Acsl3/4/5 and Cpt1b) were down-regulated in the liver, but those (Acsl3/6 and Cpt1b) in the same pathway were up-regulated in adipose tissue (FIG. 6D, FIG. 6E). This data suggests that MKRN1 ablation results in stricter regulation of fatty acids in adipose tissue by decreasing lipogenesis and increasing lipolysis with respect to the regulation of these processes in the liver, by which both lipolysis and lipogenesis are decreased.

<2-2> Confirmation of Regulatory Effect on Carbohydrate Metabolism According to Suppression of MKRN1 Expression Because it was revealed that the regulation of the MKRN1 expression had an effect on lipid synthesis and degradation in a lipid metabolism pathway, an effect of the MKRN1 suppression in carbohydrate metabolism was confirmed at a gene expression level.

In addition to lipid metabolism, carbohydrate metabolism was significantly influenced by MKRN1 ablation (FIG. A, right). In the liver, the genes involved in glycolysis (Hk1/2, Gpi1, Pfkp, Aldoa, Gapdh, Eno1, Pkm and Pklm) and gluconeogenesis (G6pc and Pck2) were down-regulated (FIG. 6D). In adipose tissue, however, the genes involved in glucose uptake (Slc2a4/Glu4) and glycolysis were up-regulated (FIG. 6E), as were those involved in lipolysis. On the other hand, lactate dehydrogenase was up-regulated in adipose tissue (Ldha), but down-regulated (Ldhb) in the liver (FIG. 6D, FIG. 6E). Glucose metabolism is linked to fatty acid metabolism through acetyl-CoA. Up- and down-regulation of glucose utilization in adipose tissue and the liver, respectively, reflect an increased amount of acetyl-CoA and, thus, a larger supply of acetyl-CoA for fatty acid biosynthesis in adipose tissue than in the liver, which might lead to the up-regulation of lipolysis in adipose tissue (FIG. 6E). Furthermore, the genes involved in BAT thermogenesis (Ucp1, Clic5, and Ppargc1a) were significantly up-regulated in MKRN1-null adipose tissue (FIG. 6C).

<2-3> Confirmation of Change in AMPK Expression Level and Regulatory Effect on Glycolysis According to Suppression of MKRN1 Expression To verify how MKRN1 affects such energy metabolism, levels of glucose uptake and lactate secretion in cells were also verified to check an effect of MKRN1 on a regulatory action of glycolysis.

Specifically, Hep2G cells were transformed with MKRN1 siRNA #6 or #7 and siAMPKα to suppress the MKRN1 expression in order to prepare cells in which MKRN1 was inhibited, and then cultured in a medium containing 10 mg of glucose. After the culturing, the cells were recovered and counted. Then, concentrations of glucose and lactate in the medium were quantified to compare the levels of glucose uptake and lactate secretion in the cells to the normal control. Also, the recovered cells were homogenized to obtain a whole cell extract (WCL), and the whole cell extract (WCL) was then subjected to immunoblotting. For the immunoblotting, an anti-AMPKα1 antibody or an anti-AMPKα2 antibody was used as the primary antibody, and an anti-mouse IgG antibody was used as the secondary antibody. Actin was selected as the control to compare the expression of the protein in the cell extract.

Figure 7:
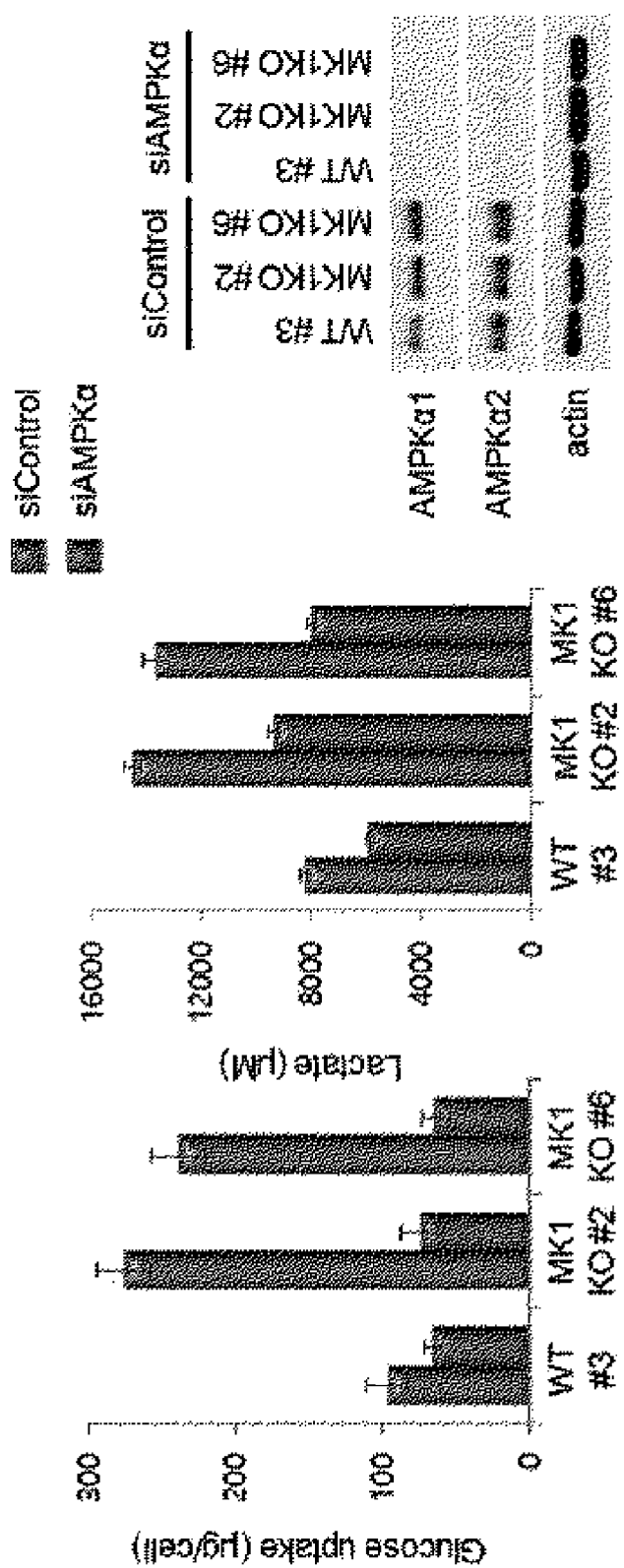
FIG. 7 shows a regulatory effect on glycolysis through the suppression of MKRN1 expression.

As a result, as shown in FIG. 7, it was confirmed that a residual concentration of glucose in the medium and a concentration of lactate secreted into the medium were significantly reduced in the MKRN1 KO cells due to an increase in activity of glycolysis, compared to the normal control, indicating that such an increase in the concentration was due to the regulation by AMPK activated when the MKRN1 was suppressed (FIG. 7).

To verify this, the AMPKα protein was also knocked down in the MKRN1 KO cells to suppress the activity of AMPK, and glucose metabolism was then checked. As a result, it was confirmed that all the glucose uptake and lactate secretion abilities which had been increased by the MKRN1 knockout were reduced again (FIG. 7). From these results, it was confirmed that the MKRN1 was a novel factor capable of regulating energy metabolism in the cells, which was achieved through a mechanism for degrading AMPK as the E3 ligase for AMPK.

<2-4> Regulation of mTOR Signaling Process According to MKRN1 and AMPK mTOR signaling was previously shown to be one of the main targets of AMPK. Analyses of the mTOR pathway showed that mTOR and its upstream (Hras, Mapk3, Pik3r1 and Rheb) and downstream (Eif4e, Sgk1, Pparg and Srebf1) genes were down-regulated in the liver, while its upstream (Pik3r1/3, Pik3cb and Akt2) and downstream (Rps6kb2, Eif4e, Prkca/g and Pparg) genes were down-regulated in adipose tissue (9). These findings suggest that the activation of AMPK by MKRN1 ablation negatively regulates mTOR signaling in the liver and adipose tissue. Taken together, this data suggests systematic customized regulation of fatty acid and glucose metabolism in the liver and adipose tissue by MKRN1 and AMPK.

Figure 8A:
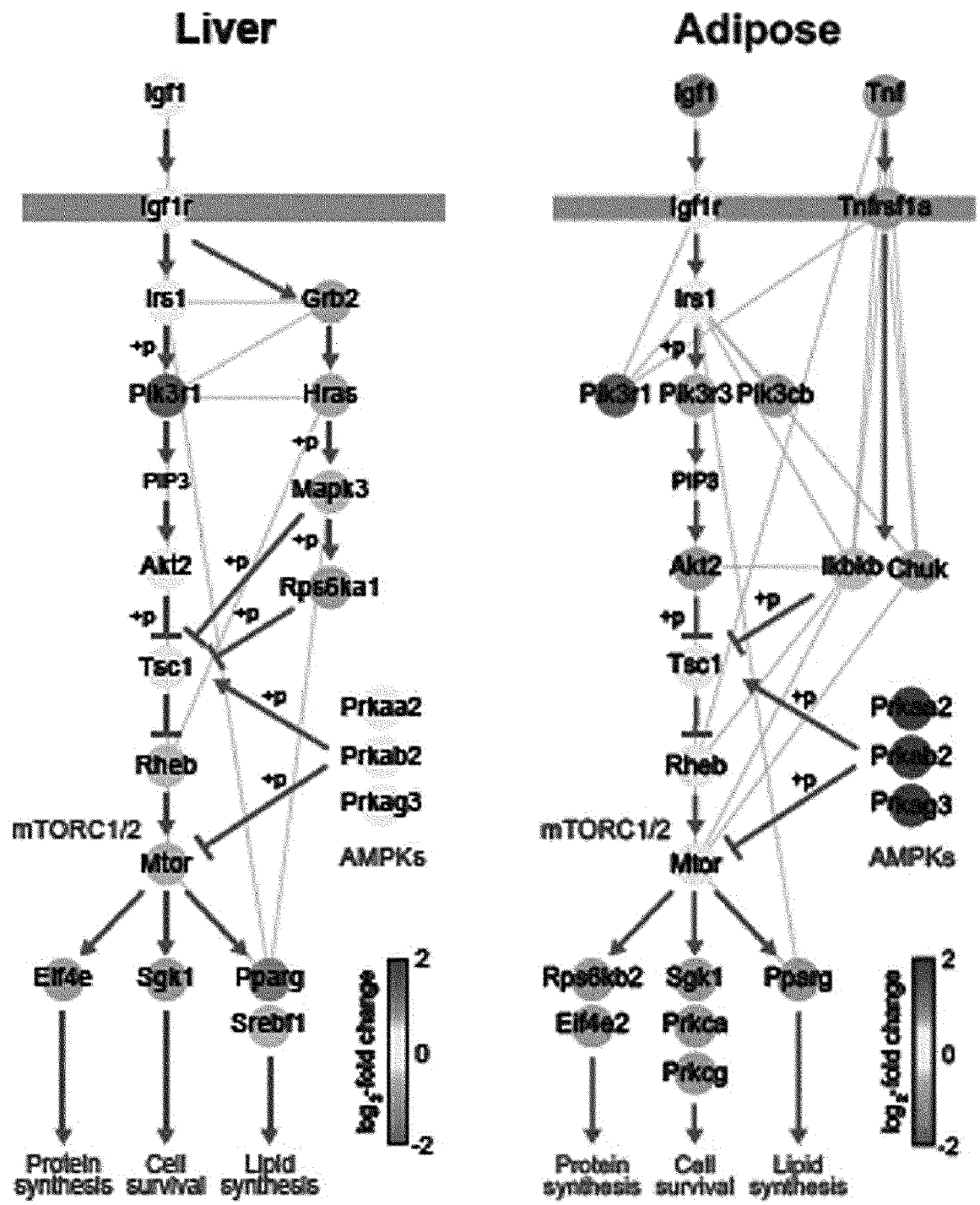
FIGS. 8A and 8B show the regulation of mTOR signaling by MKRN1 and AMPK, i.e., a network model describing alterations of mTOR signaling in MKRN1-knockout liver (left) and adipose tissues (right): Arrows denote positive regulation in signaling cascades, while inhibition symbols denote negative regulation. Node colors represent up-(red) or down-regulation (green) in MK1−/− liver or adipose tissues (A). The color bar represents the gradient of the log 2-fold-changes of mRNA expression levels following MKRN1 ablation relative to those in WT (B)
Figure 8B:
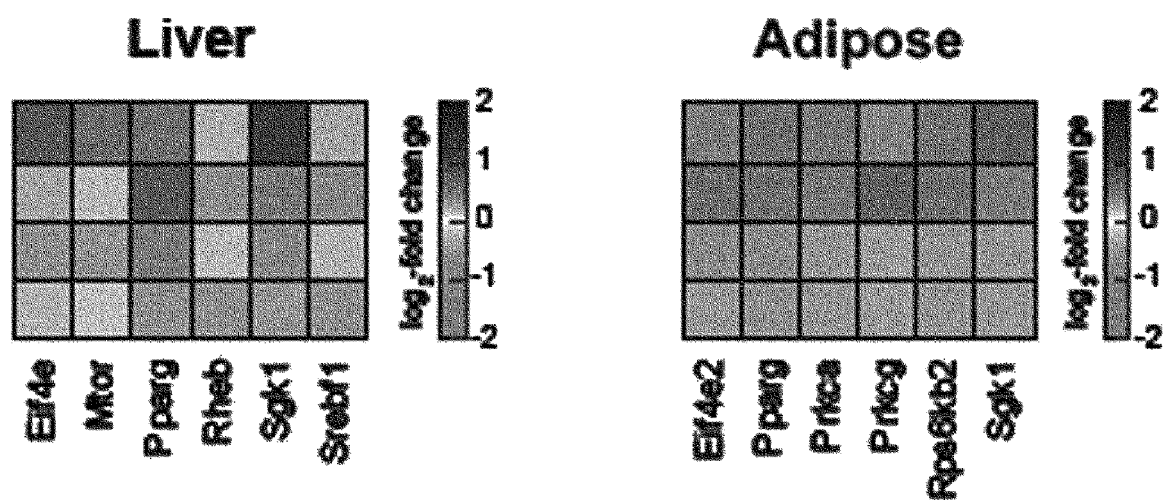

Functional enrichment and network analyses revealed the differential regulation of AMPK, mTOR and fatty acid and glucose metabolism between the liver and adipose tissue. Although we showed that AMPKs were regulated at the protein level by MKRN1, the mRNA expression levels of Prkaa2/AMPK□2, Prkab2/AMPK□2, and Prkag3/AMPK□3 were increased in adipose tissue by MKRN1 ablation but showed no change in the liver, suggesting that there are additional metabolic needs to be accommodated by the increases of AMPKs, even at the mRNA level in adipose tissue (FIG. 8A, FIG. 8B). In mTOR signaling, the MAPK pathway (Hras, Mapk3, Pik3r1 and Rheb) and its upstream and downstream factors (Eif4e, Sgk1, Pparg and Srebf1) were predominantly down-regulated in the liver, while the PI3K-AKT pathway (Pik3r1/3, Pik3cb and Akt2) and its downstream factors (Rps6kb2, Eif4e, Prkca/g and Pparg) were predominantly down-regulated in adipose tissue (FIG. 8A and FIG. 8B). Although Ppar is one of the major transcription factors involved in lipid metabolism, there was no apparent change in the expression of Ppar in the liver or adipose tissue. We cannot, however, exclude the possibility that MKRN1 regulates Ppar at the post-translational level, since Ppar is known to be a target of MKRN1. Further studies are required to address this issue in the future. Although lipogenesis was consistently down-regulated in both the liver and adipose tissue, the catabolism of fatty acids and glucose was up-regulated in adipose tissue but down-regulated in the liver, indicating the differential regulation of metabolic pathways in MKRN1-null mice.

Taken together, the differential regulation of the above processes by MKRN1 might be ascribed to additional metabolic needs arising from the increased uptake and utilization of glucose in adipose tissue.

Example 3

Confirmation of Inhibitory Effect on Obesity in MKRN1-Knockout Mice

<3-1> Confirmation of Effect of MKRN1 Suppression on Obesity by High-Fat Diet

To verify an effect of MKRN1 on metabolic diseases, first of all, it was verified whether an inhibitory effect of the MKRN1 suppression on obesity induced by a high-fat diet (HFD) could be exhibited in an obese mouse model.

Specifically, MKRN1$^{+/+}$ (WT) C57/BL6 mice and MKRN1$^{-/-}$ (KO) C57/BL6 mice were prepared, and freely fed high-fat (60%) feed when the mice were 6 weeks old. Then, the mice were bred for 16 weeks under the same environment to prepare an MKRN1$^{+/+}$ (WT) obese mouse model group and an MKRN1$^{-/-}$ (KO) obese mouse model group. From the beginning date of high-fat diet supply, body weights and average daily feed amounts of the mice in the mouse model groups were checked. After 16 weeks from the beginning of feeding, blood was also collected from the mouse model groups to check a blood leptin concentration.

Figure 9A:
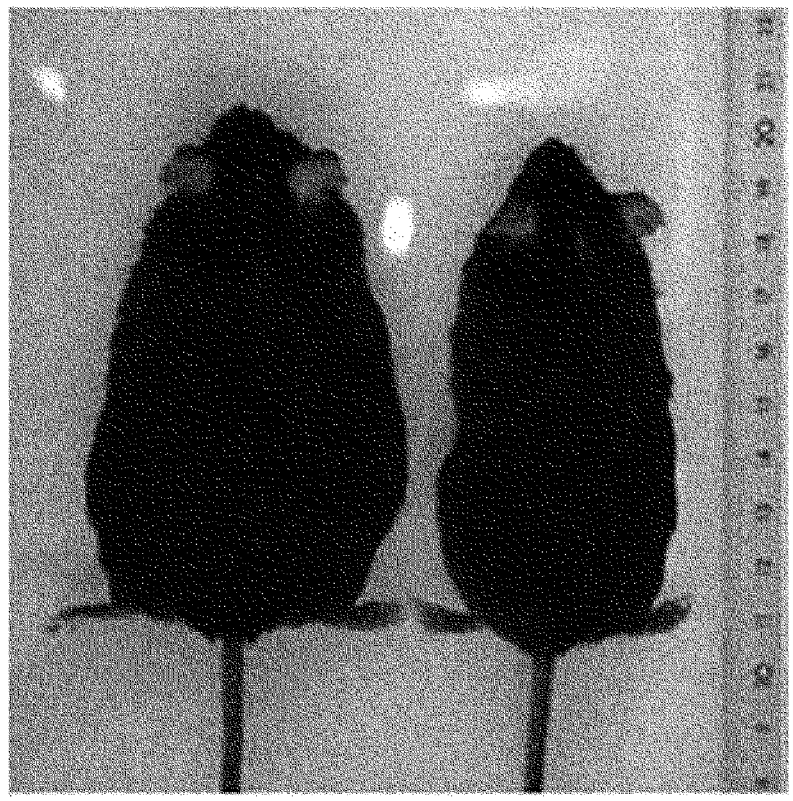
FIGS. 9A through 9D are diagrams for confirming an inhibitory effect on obesity in MKRN1-knockout mice.
Figure 9B:
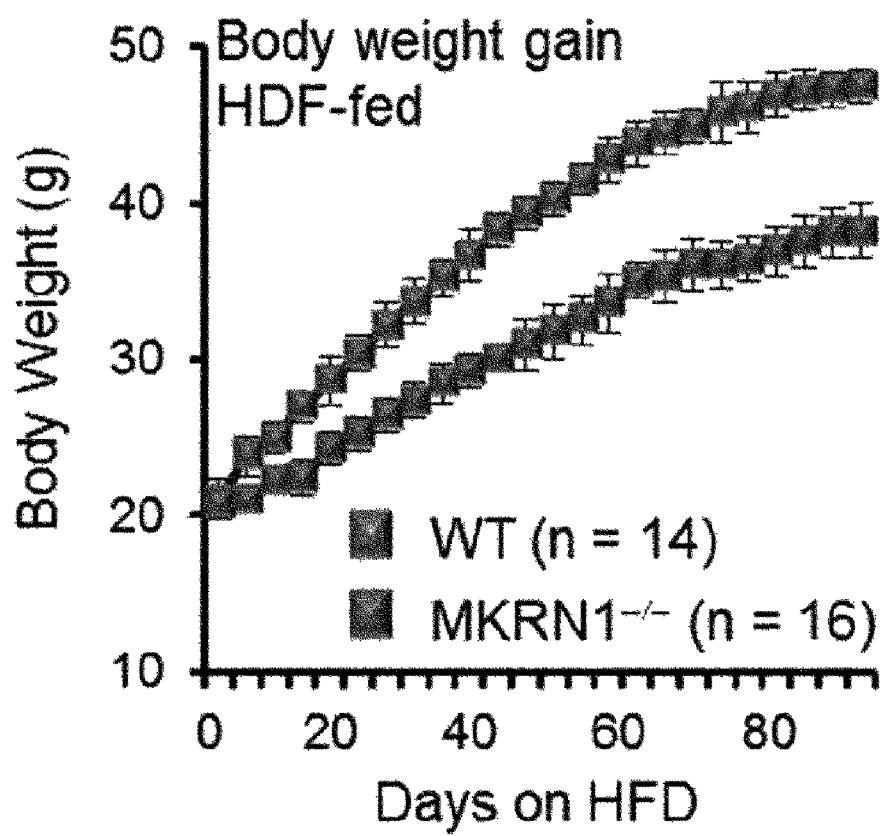
Figure 9C:
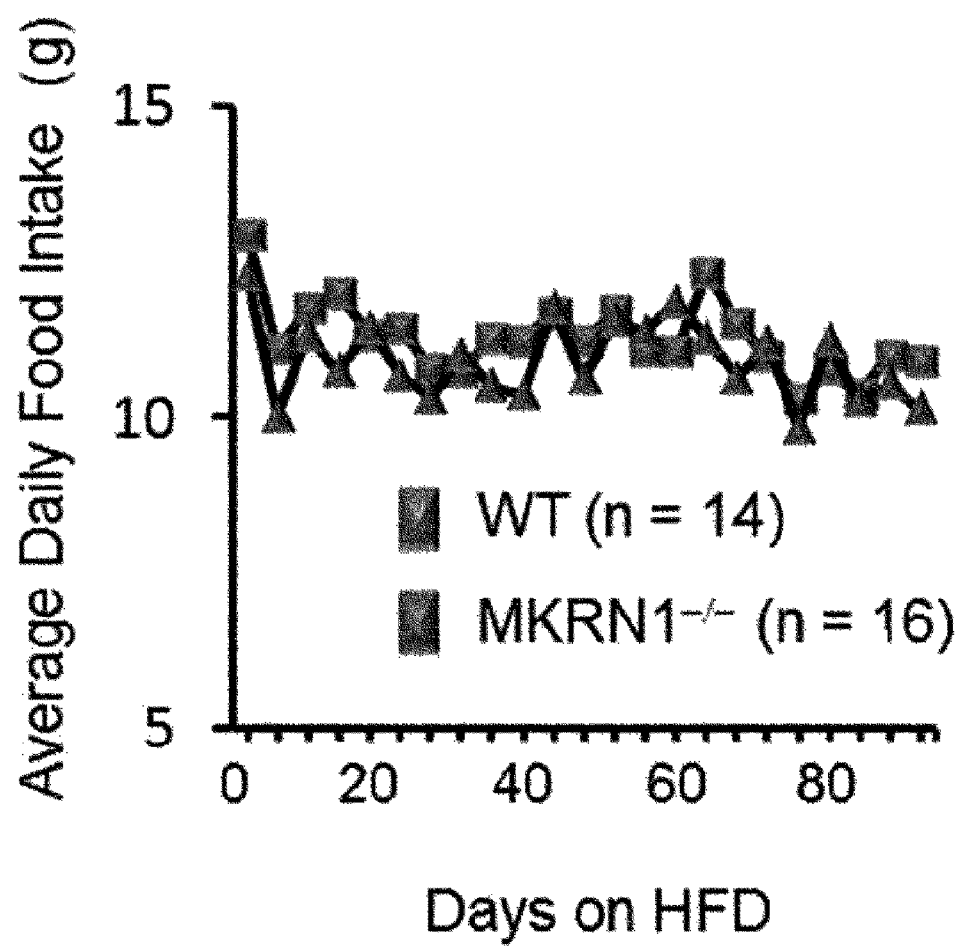
Figure 9D:
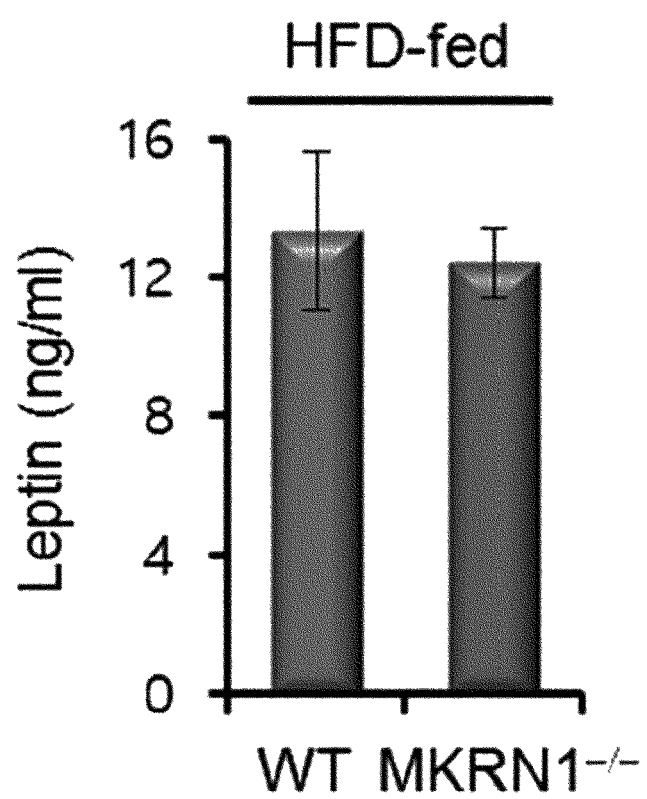

As a result, as shown in FIG. 9, it was confirmed that there was no significant difference in feed uptake between the MKRN1$^{+/+}$ (WT) and MKRN1$^{-/-}$ (KO) obese mouse model groups (FIG. 9C), and there was also no significant difference in blood concentrations of leptin which is a factor regulating feed uptake (FIG. 9D), but the body weights and fat masses of the mice increased due to the HFD-induced obesity in the MKRN1$^{+/+}$ (WT) obese mouse group, and the body weights and fat masses of the mice, which had increased due to the obesity, were highly reduced in the MKRN1$^{-/-}$ (KO) obese mouse group (FIGS. 9A and 9B). From these results, it was confirmed that the suppression of HFD-induced obesity by the AMPK signaling pathway activated by the MKRN1 knockout appeared to be effective.

<3-2> Confirmation of Effect of MKRN1 Suppression on Adipose Tissue and Fats by Means of High-Fat Diets Because it was confirmed that there was no significant difference in feed uptake due to a high-fat diet (HFD) in the obese mouse model upon the suppression of MKRN1 but an effect of reducing the body weight was expressed, the role of MKRN1 was more specifically examined by checking obesity induced by the HFD and a change in adipose tissues.

Specifically, after the 16-week breeding of the mice in the MKRN1$^{+/+}$ (WT) obese mouse model group and the MKRN1$^{-/-}$ (KO) obese mouse model group prepared in Example <3-1> was terminated, the mice in each of the mouse model groups were subjected micro CT imaging in order to check adipose tissues in their bodies. Also, the mice in each of the mouse model groups were sacrificed to obtain adipose tissues, and body weights and areas of the adipose tissues were measured. In addition, the presence of brown adipose tissues (BATs) from the adipose tissues of the sacrificed mice in the mouse model groups was checked, and then observed after H&E staining. Further, a triglyceride concentration, a total cholesterol concentration and a LDL cholesterol concentration in blood samples of the sacrificed mice in the mouse model groups were analyzed and compared.

Figure 10A:
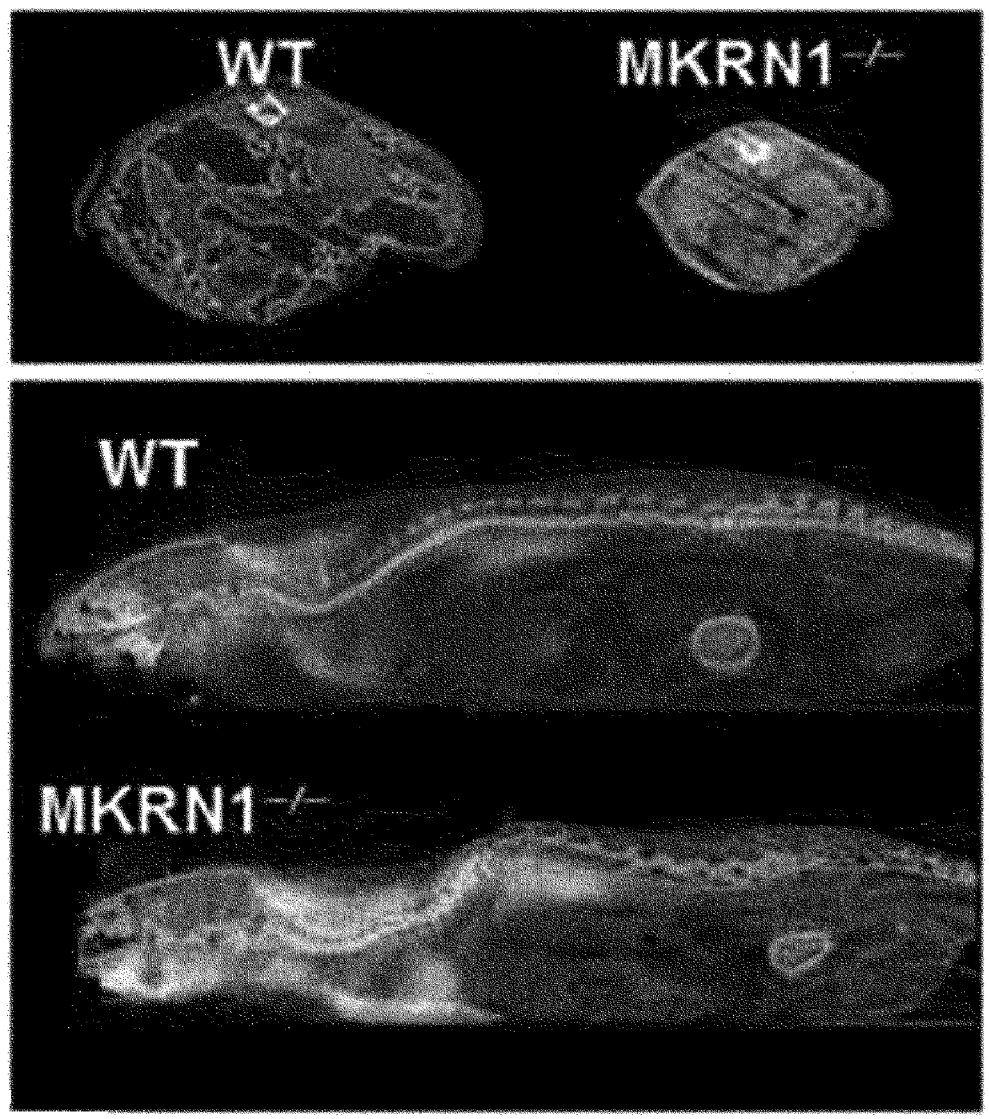
FIGS. 10A through 10F are diagrams for confirming an effect of the suppression of MKRN1 on adipose tissues and fats by high-fat diets.
Figure 10B:
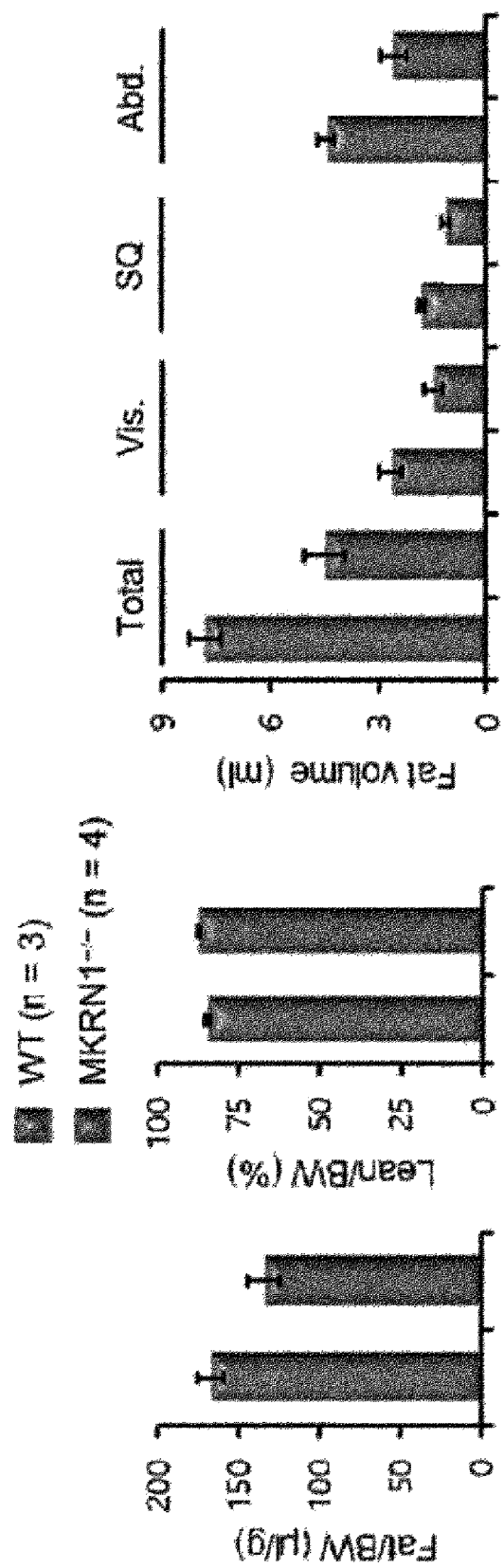
Figure 10C:
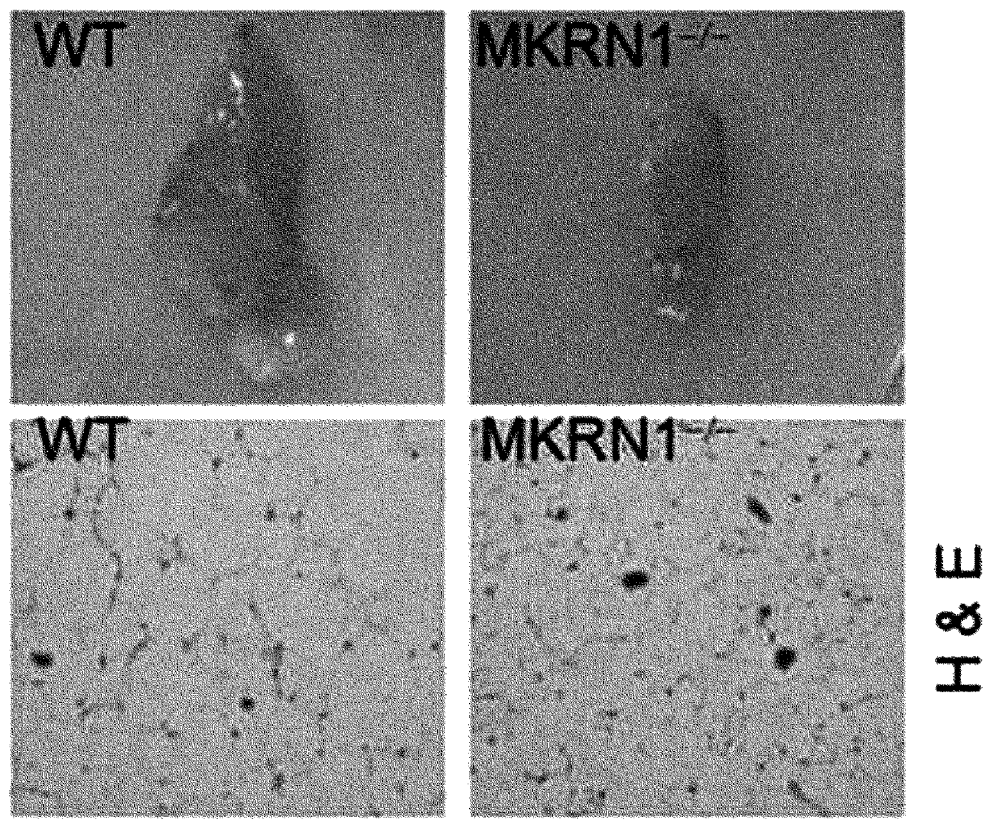
Figure 10D:
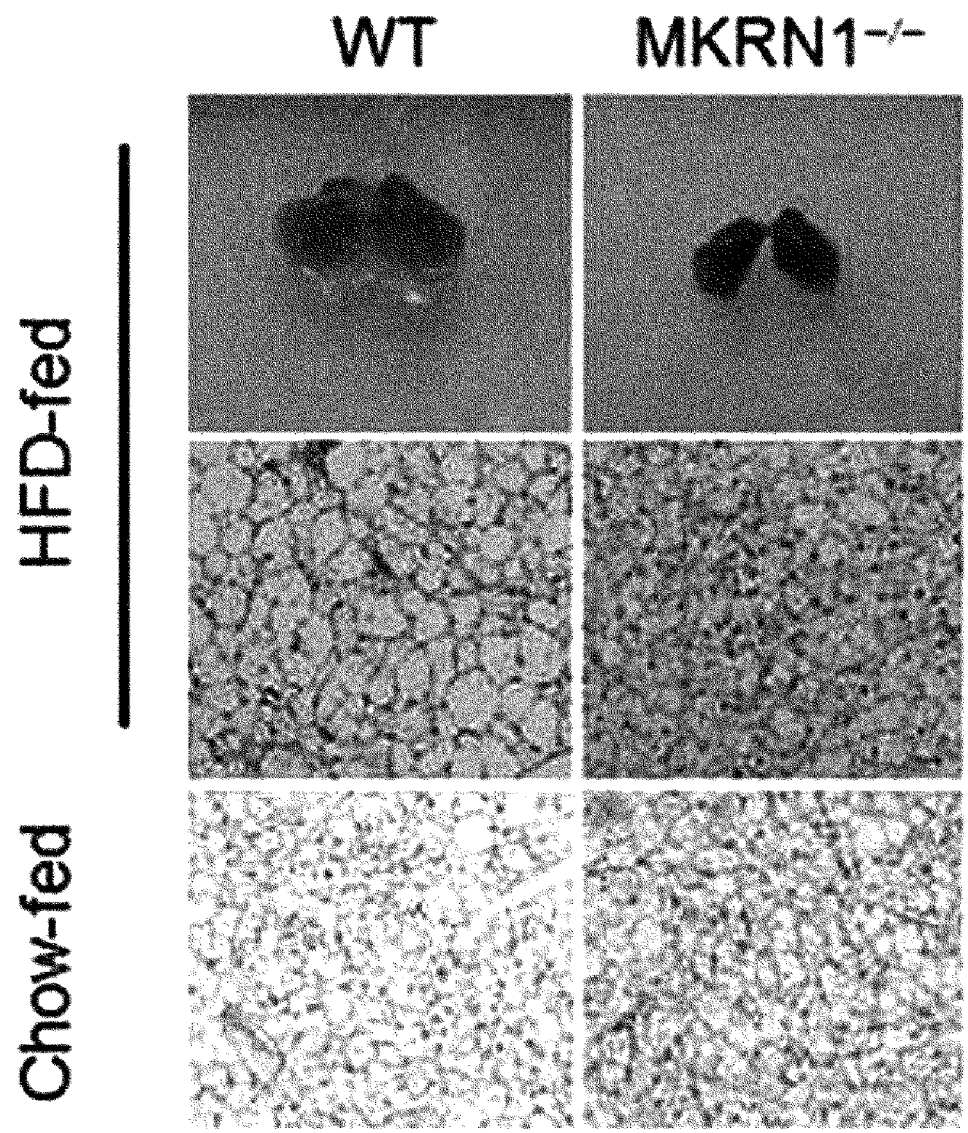

As a result, as shown in FIG. 10, it was confirmed that the size of the adipose tissues in the MKRN1$^{-/-}$ (KO) obese mouse group was significantly reduced (FIGS. 10A to 10C). Also, it is known that BAT may play a good role in burning fats through calorie consumption as it appears dark brown. From these facts, it was confirmed that the size of the brown adipose tissues (BATs) increased and the BATs looked less brown as the fats were deposited on the BATs during the HFD, which lead to obesity. However, it is known that the deposition of fats in the brown adipose tissues (BATs) was inhibited in the case of the MKRN1 KO mouse group and the brown color of the BATs was well maintained when the BATs were observed, indicating that the MKRN1$^{-/-}$ (KO) mice were highly resistant to obesity induced by the HFD (FIG. 10D).

Figure 10E:
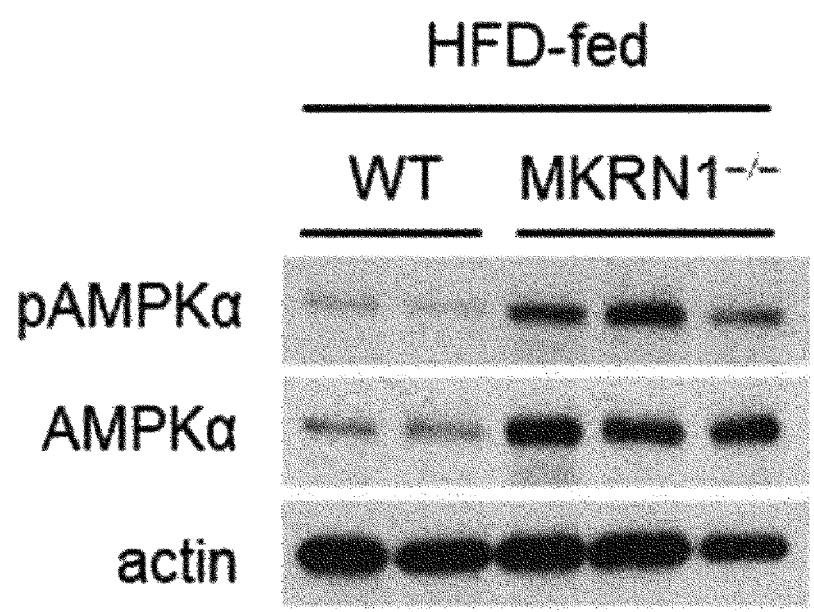
Figure 10F:
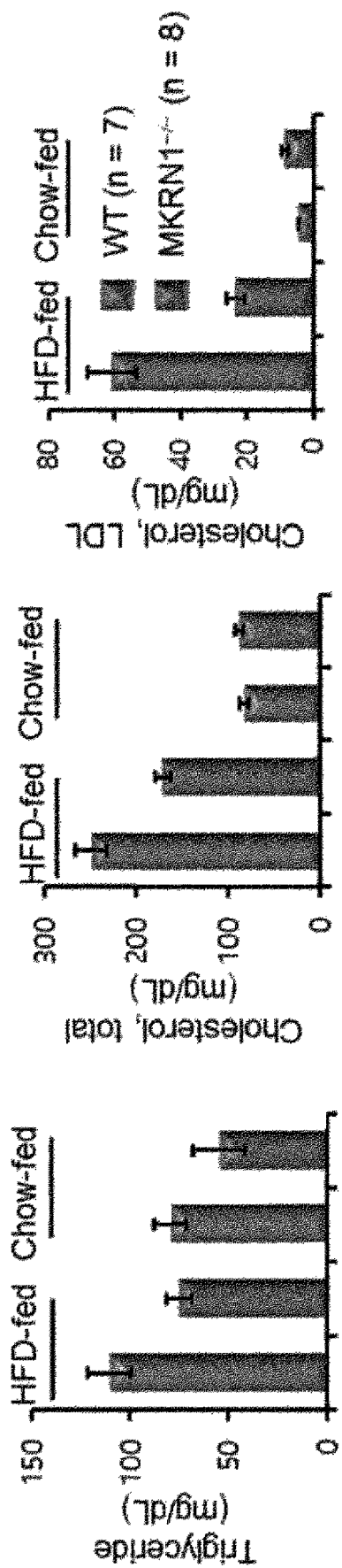

Moreover, it was confirmed that a protein level and a phosphorylation level of AMPK significantly increased in the adipose tissues of the mice in the obese mouse model, compared to the obese mice in which MKRN1 was normally expressed due to MKRN1 KO (FIG. 10E). Also, it was confirmed that the blood triglyceride and cholesterol levels in the MKRN$^{-/-}$ (KO) mice were able to be significantly reduced, indicating that the MKRN1 suppression could be effective in preventing secondary metabolic diseases (FIG. 10F).

Example 4

Confirmation of Improving Effect on Diabetes in MKRN1-Knockout Mice

To examine an effect of MKRN1 on metabolic diseases, it was examined whether the MKRN1 suppression was effective in alleviating diabetes in a model of type 2 diabetes (insulin resistance acquired) induced by HFD.

Specifically, MKRN1$^{+/+}$ (WT) C57/BL6 mice and MKRN1$^{-/-}$ (KO) C57/BL6 mice were prepared, and freely fed high-fat (60%) feed when the mice were 6 weeks old. Then, the mice were bred for 16 weeks under the same environment to prepare an MKRN1$^{+/+}$ (WT) diabetic mouse model group and an MKRN1$^{-/-}$ (KO) diabetic mouse model group. After 16 weeks from the beginning of feeding, blood was also collected from the diabetic mouse model groups to check a blood sugar level. Also, the mice in each of the diabetic mouse model groups were fasted for 16 hours. At the same time, a glucose tolerance test (GTT) was carried out by measuring blood sugar levels at 0, 15, 30, 60 and 120 minutes from the beginning of fasting.

Figure 11A:
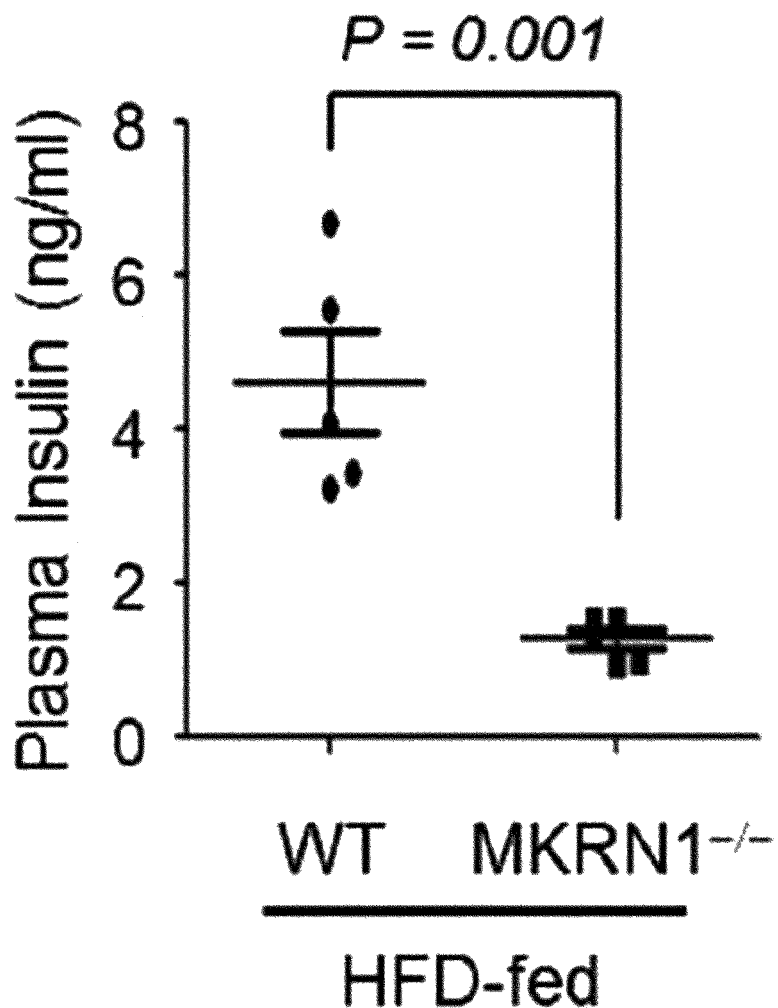
FIGS. 11A through 11B are diagrams for confirming an improving effect on diabetes in MKRN1-knockout mice.
Figure 11B:
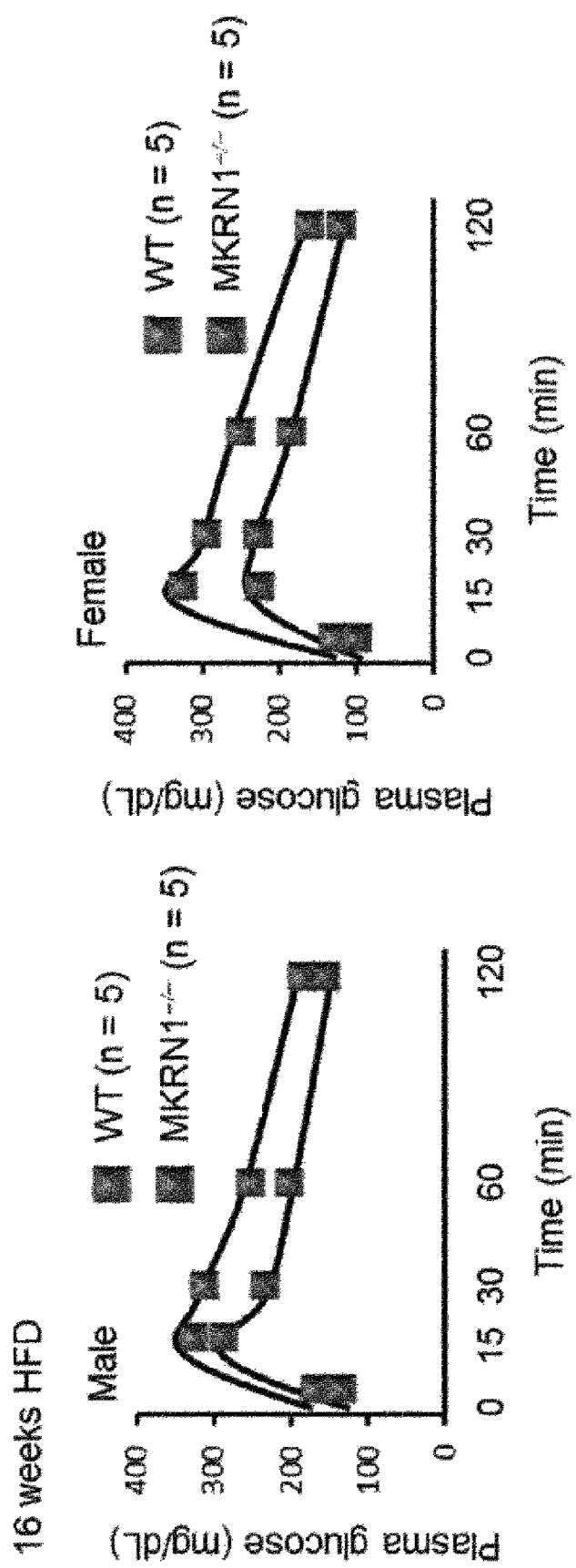

As a result, as shown in FIG. 11, it was confirmed that hyperinsulinemia induced by the HFD was significantly alleviated in the MKRN1$^{-/-}$ (KO) diabetic mouse group, compared to the MKRN1$^{+/+}$ (WT) diabetic mouse group (FIG. 11A). Also, it was confirmed that diabetic diseases were significantly alleviated in the MKRN1$^{-/-}$ (KO) diabetic mouse group, compared to the MKRN1$^{+/+}$ (WT) diabetic mouse group (FIG. 11B). From these results, it was confirmed that the regulation of AMPK signaling by the MKRN1 may have a great influence on representative metabolic diseases.

Example 5

Confirmation of Improving Effect on Fatty Liver in MKRN1-Knockout Mice

<5-1> Confirmation of Effect of MKRN1 in a Model of Fatty Liver Induced by High-Fat Diets To examine an effect of MKRN1 on metabolic diseases, it was examined whether the MKRN1 suppression was effective in improving fatty liver in a model of fatty liver induced by HFD.

Specifically, MKRN1$^{+/+}$ (WT) C57/BL6 mice and MKRN1$^{-/-}$ (KO) C57/BL6 mice were prepared, and freely fed high-fat (60%) feed when the mice were 6 weeks old. Then, the mice were bred for 16 weeks under the same environment to prepare an MKRN1$^{+/+}$ (WT) fatty liver mouse model group and an MKRN1$^{-/-}$ (KO) fatty liver mouse model group. After 16 weeks from the beginning of feeding, the mice in each of the fatty liver model groups were sacrificed to obtain hepatic tissues, and body weights and areas of the hepatic tissues were measured. Also, after the deposition of fats in hepatocytes of the hepatic tissues was checked, the hepatic tissues were hydrolyzed to obtain a liver lysate sample. The total cholesterol level in the liver lysate sample was determined, and subjected to Western blotting to determine expression and phosphorylation levels of AMPKα. In addition, hepatic function tests (AST and ALT) were carried out using the liver lysate sample.

As a result, it was confirmed that the livers extracted from the MKRN1$^{+/+}$ (WT) fatty liver mouse group had a typical fatty liver phenotype in which the sizes and weights of the livers increased and the livers were more paler and whiter than the typical livers as fats were deposited in the livers, as shown in FIG. 12. On the other hand, it was confirmed that the livers extracted from the MKRN1$^{-/-}$ (KO) fatty liver mouse group had a significantly smaller size, and also weights recovered to a normal level, and that MKRN1 KO was able to control fatty liver induced by the HFD because the color of the livers was kept in a healthy state (FIG. 12A).

Figure 12A:
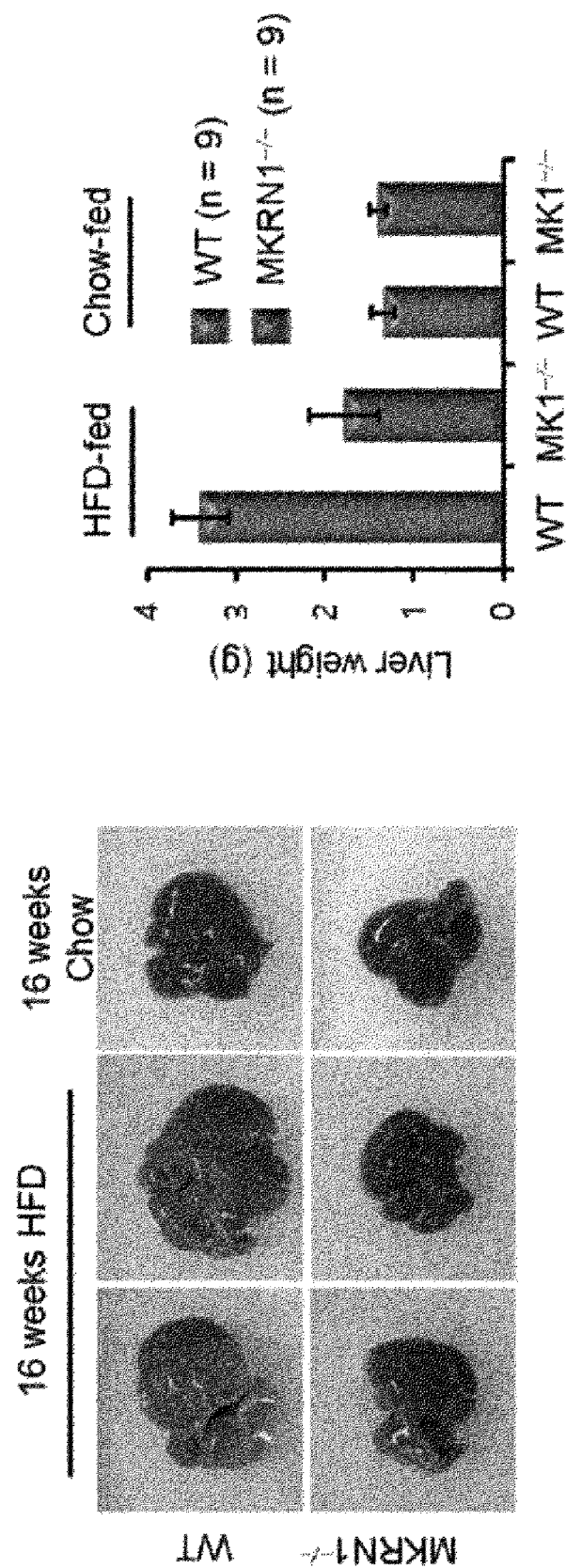
FIGS. 12A through 12F are diagrams for confirming an effect of MKRN1 on fatty liver.
Figure 12B:
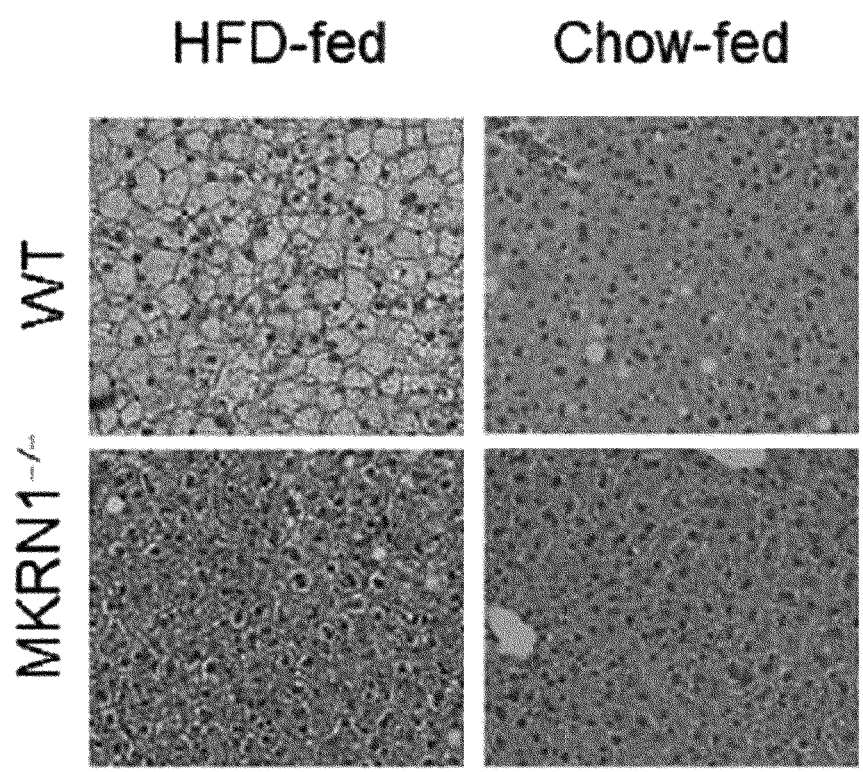
Figure 12C:
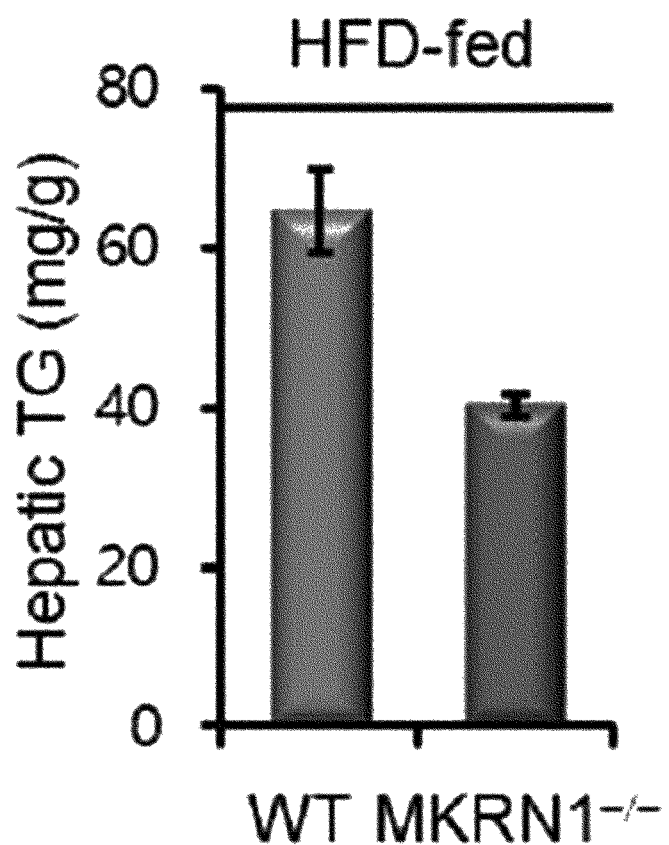
Figure 12D:
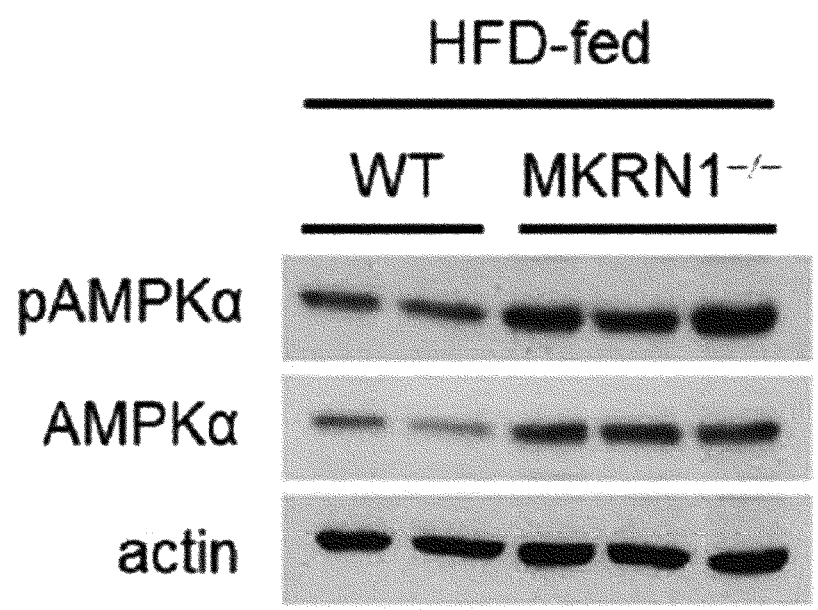
Figure 13:
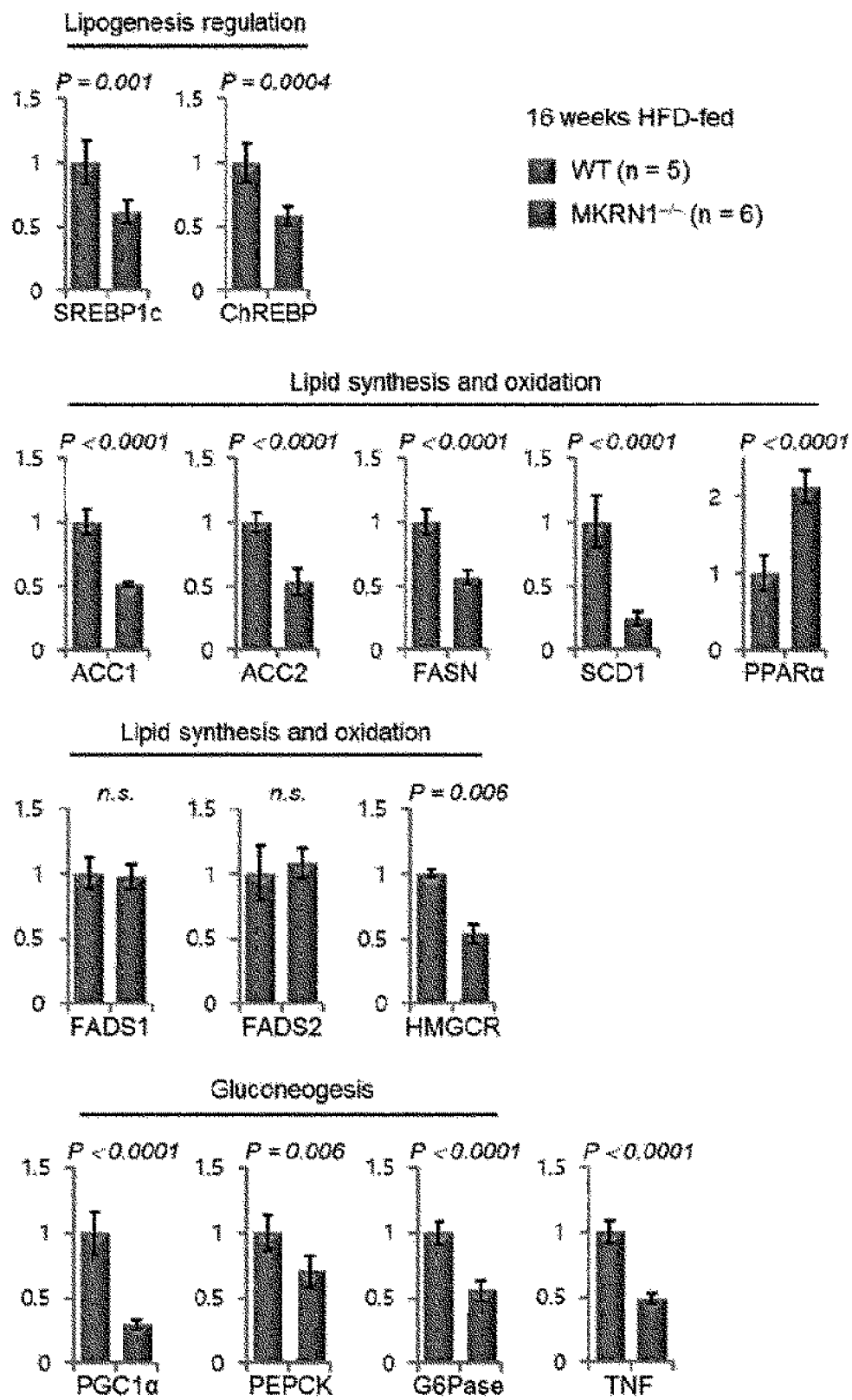
FIG. 13 is a diagram for confirming an effect of MKRN1 KO on an AMPK signaling pathway in the hepatocytes.
Figure 14A:
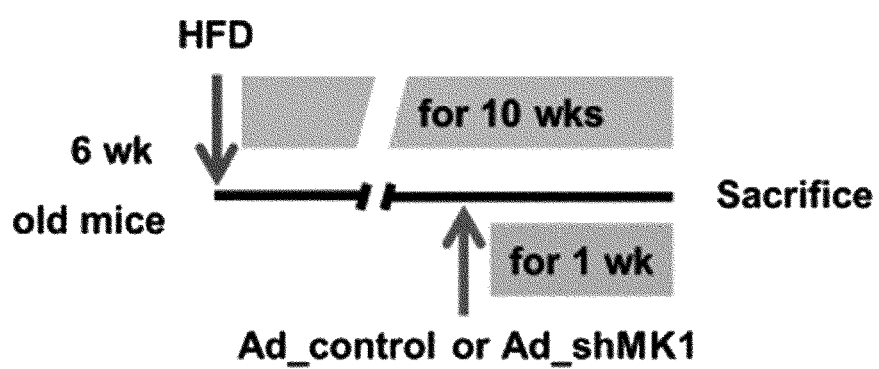
FIGS. 14A through 14K show that adenovirus-mediated knockdown of hepatic MKRN1 improves hepatic steatosis in diet-induced obese mice.
Figure 14B:
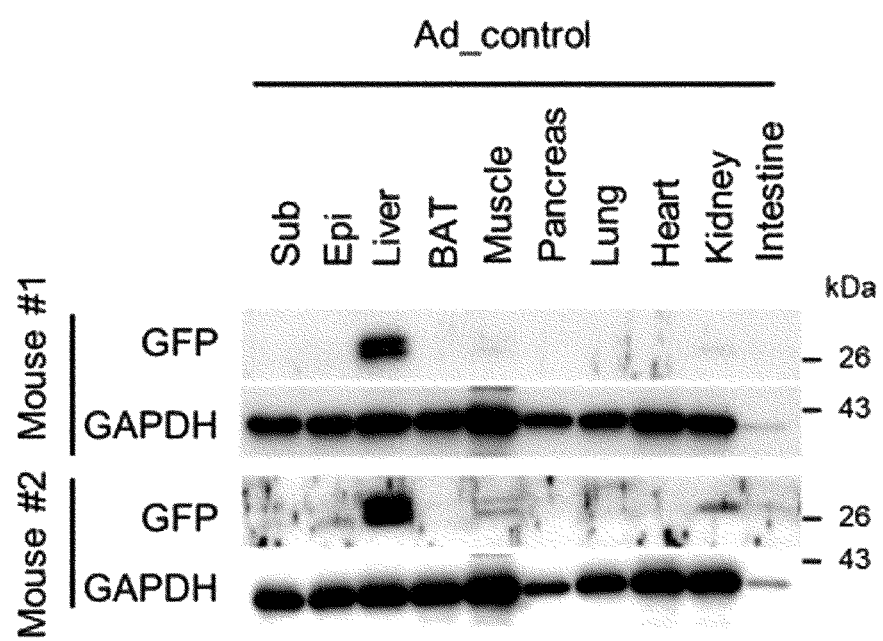
Figure 14C:
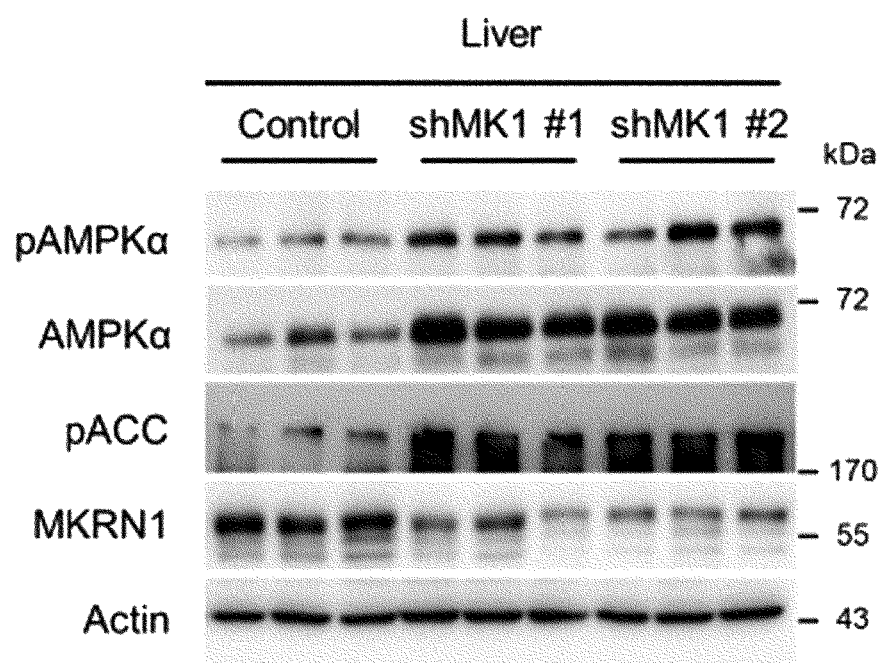
Figure 14D:
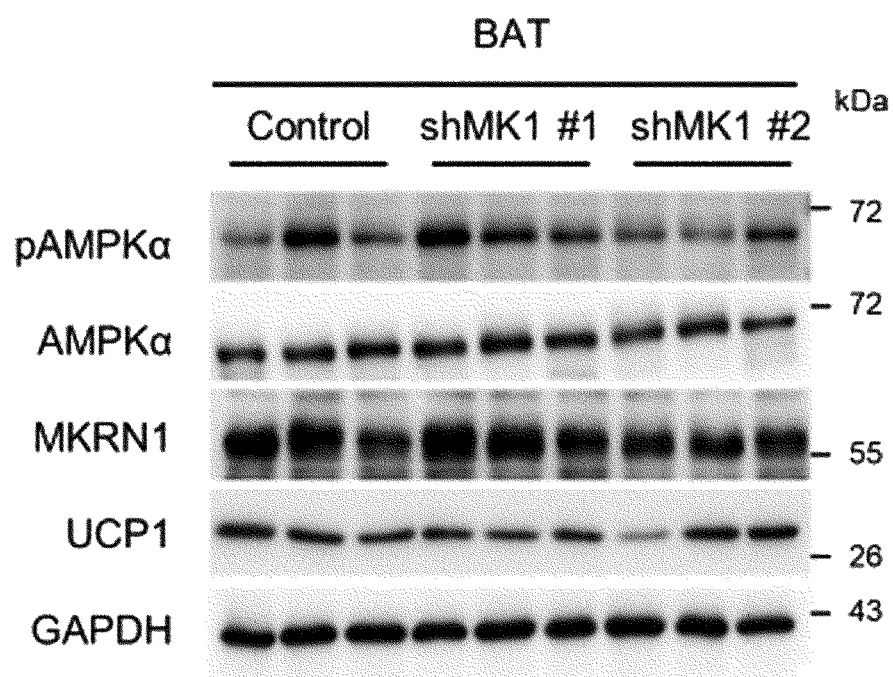
Figure 14E:
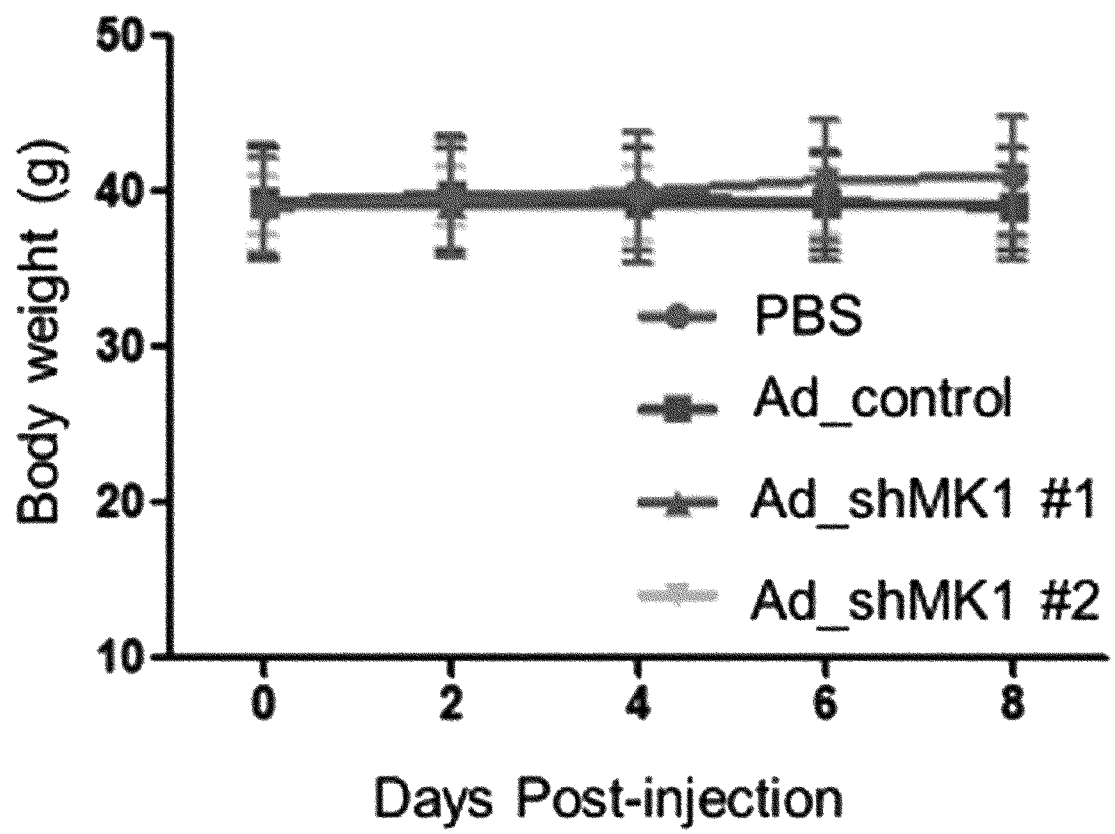
Figure 14F:
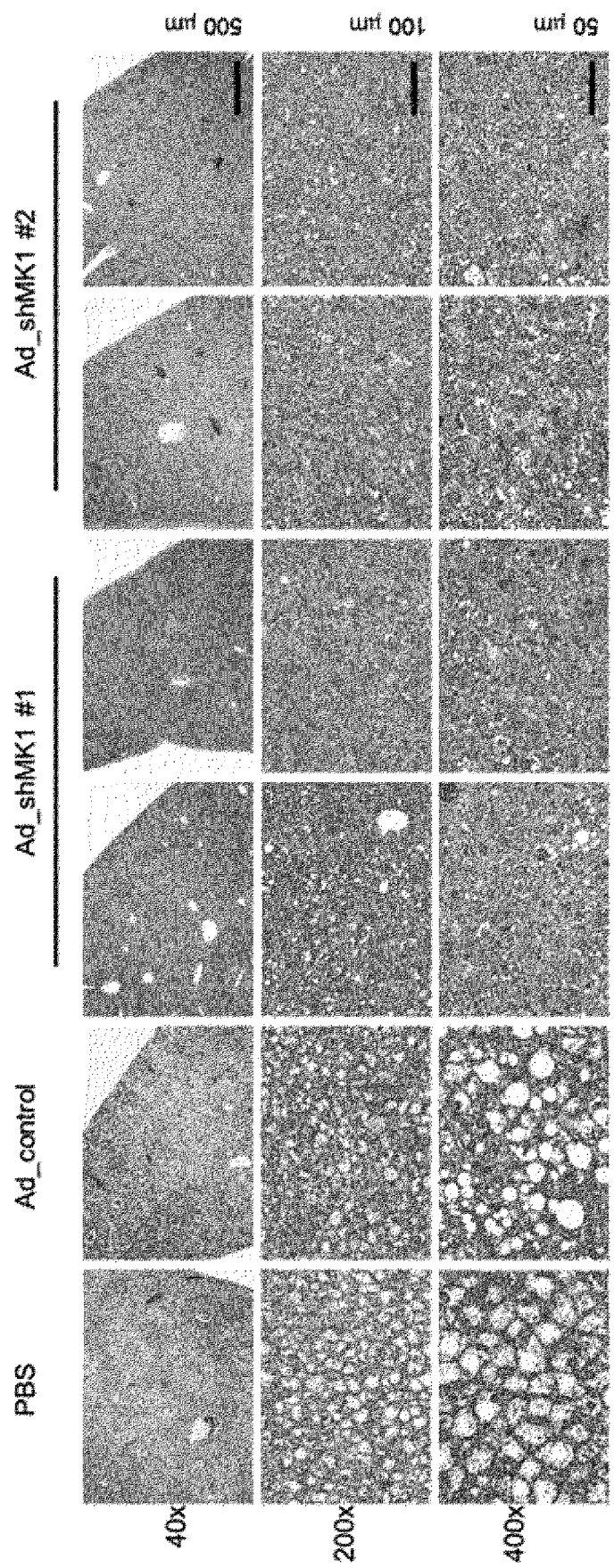
Figure 14G:
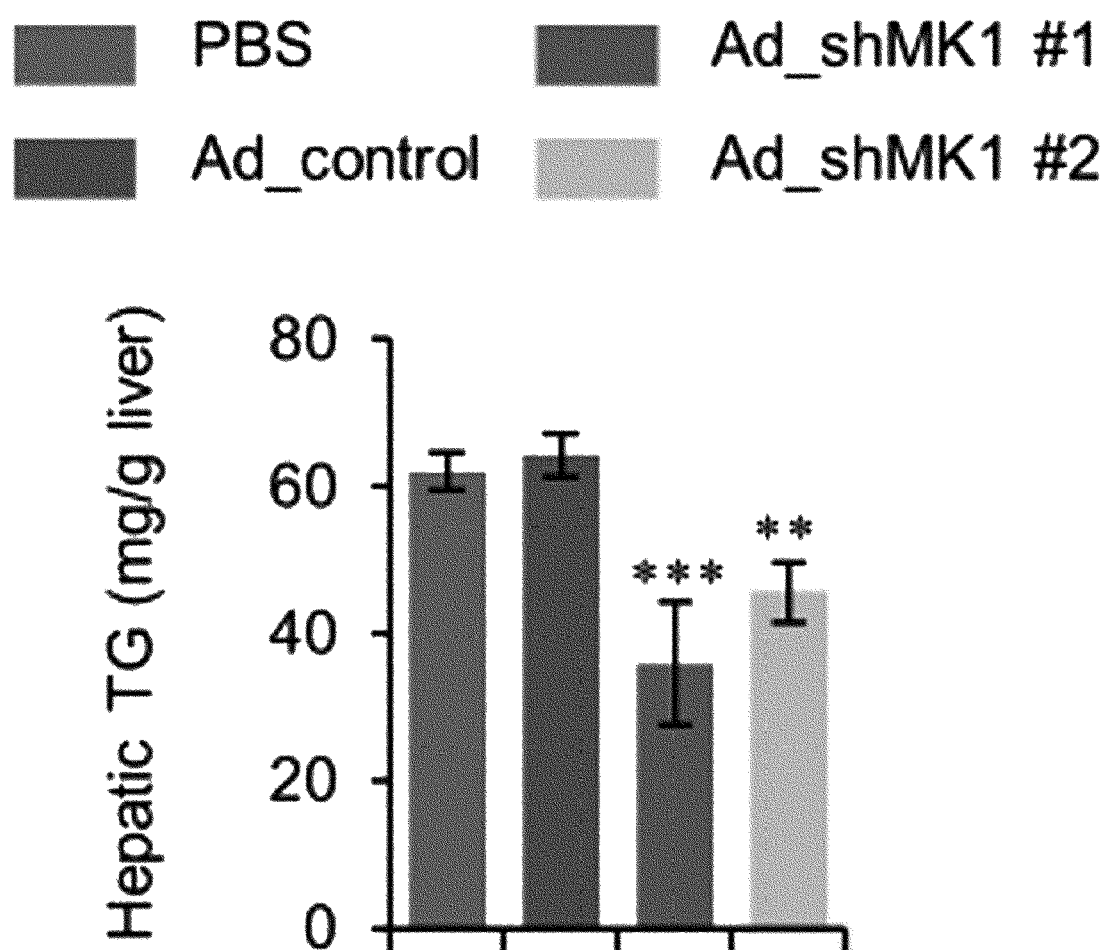
Figure 14H:
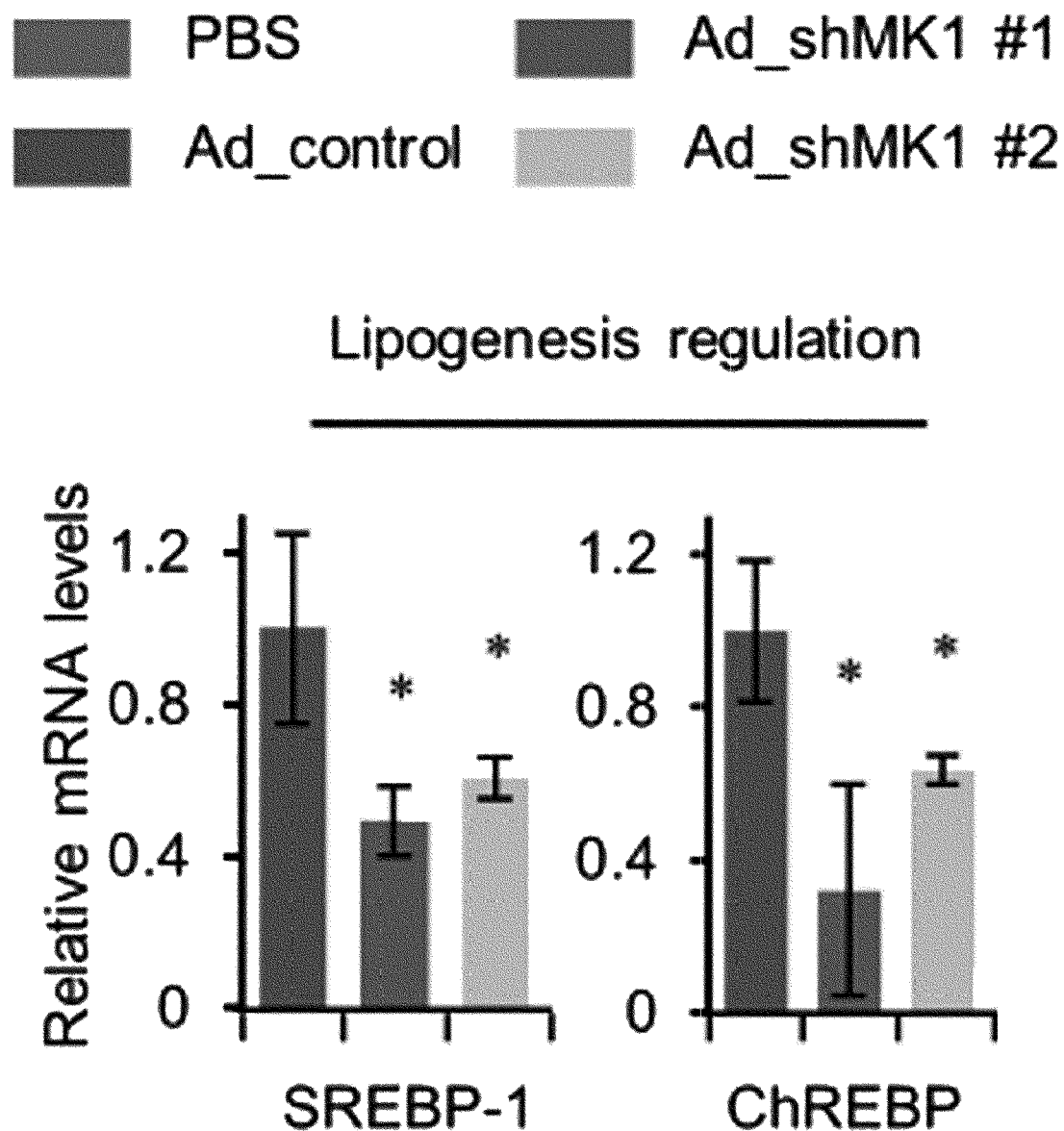
Figure 14I:
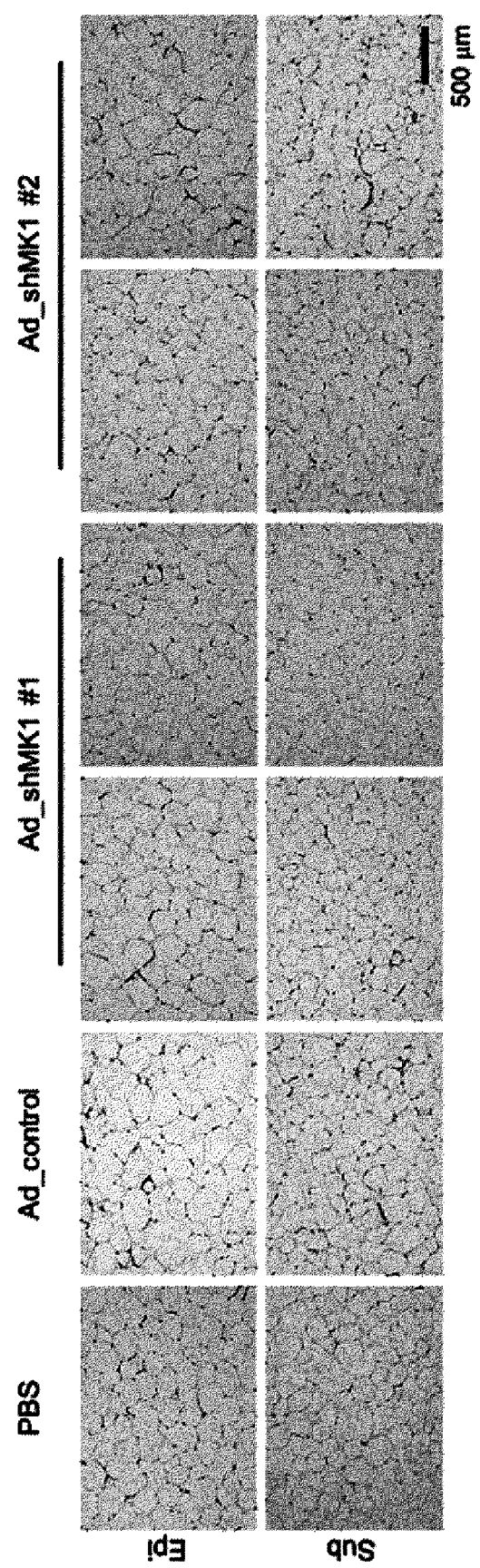
Figure 14J:
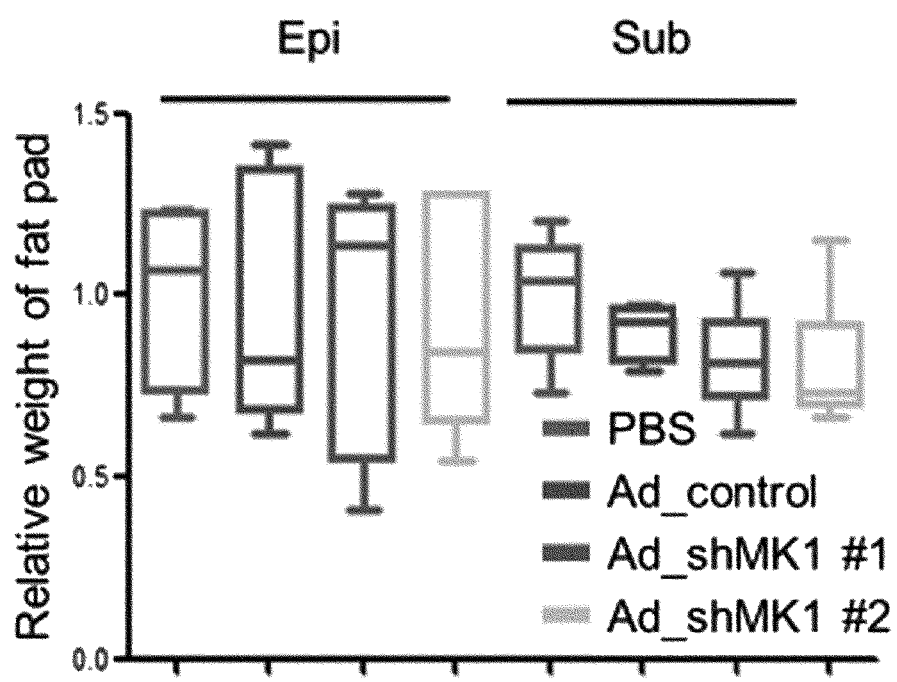
Figure 14K:
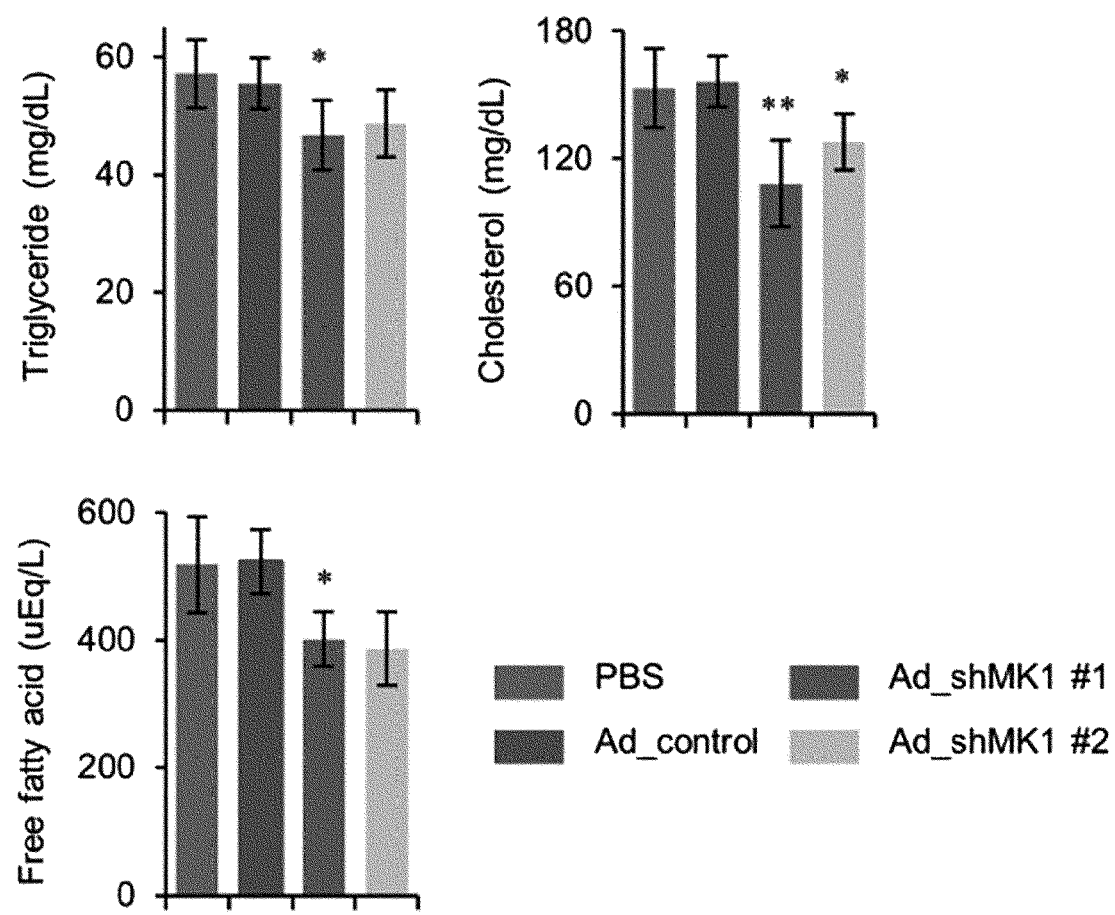

From the histological results determined through H&E staining, it was also confirmed that the deposition of fats in the hepatocytes was reduced in the MKRN1$^{-/-}$ (KO) fatty liver mouse group, compared to the MKRN1$^{+/+}$ (WT) fatty liver mouse group (FIG. 12B), the concentration of triglycerides also decreased (FIG. 12C), and the expression and phosphorylation levels of the AMPK protein increased (FIG. 12D). From these results, it was confirmed that MKRN1 KO strongly inhibited fatty liver.

Figure 12E:
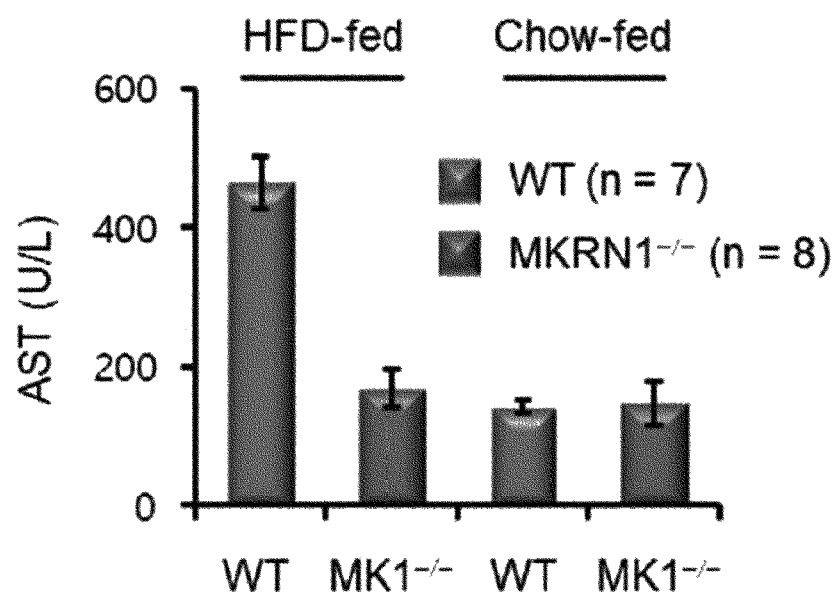
Figure 12F:
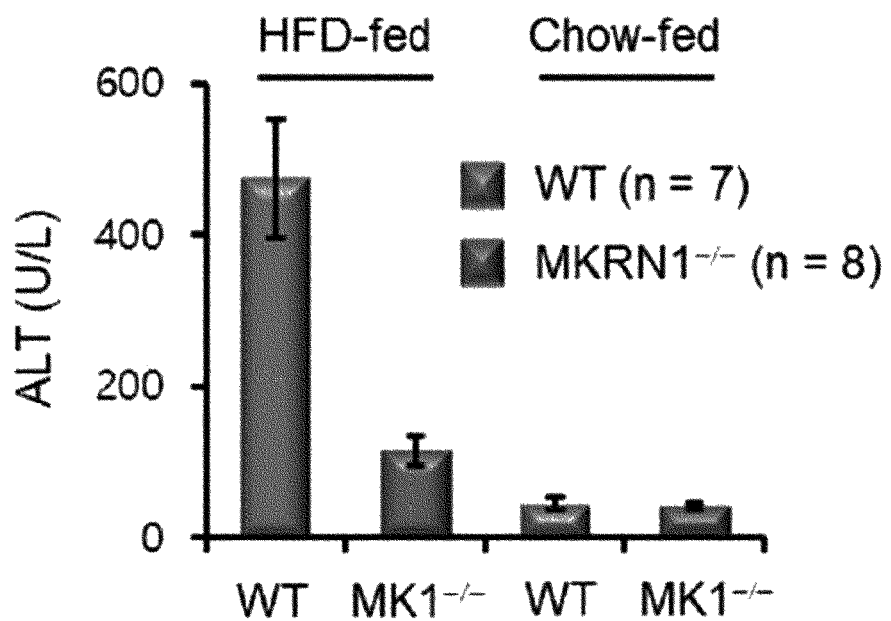

In addition, because liver damage may be caused due to hepatic dysfunction when fatty liver lasts for a long time, hepatic function tests for AST and ALT were carried out. As a result, it was confirmed that fatty liver was inhibited in the MKRN1$^{-/-}$ (KO) fatty liver mouse group, indicating that the liver damage caused by fatty liver was significantly improved (FIGS. 12E and 12F). From these results, it was confirmed that the MKRN1 suppression induced the activity of AMPK and highly inhibited fatty liver induced by the high-fat diets.

<5-2> Confirmation of Effect of MKRN1 KO on AMPK Signaling Pathway in Hepatocytes To determine whether an AMPK signaling pathway was activated in hepatocytes in the MKRN1$^{-/-}$ (KO) fatty liver mouse group and energy metabolism is regulated through the activation, expression levels of a group of genes known as genes targeting AMPK signaling were measured.

Specifically, as carried out in Example <5-1>, a fatty liver mouse model was prepared, and hepatic tissues extracted from the fatty liver mouse model were hydrolyzed to prepare a liver lysate sample. Thereafter, the total intracellular mRNA was isolated and extracted from the liver lysate sample, and then subjected to reverse transcription PCR (RT-PCR) to synthesize cDNA. Then, real-time PCR was carried out using the synthesized cDNA sample as a template and using respective primers to amplify the SREBP1, chREBP, ACC1, ACC2, FASN, SCD1, PPARα, FADS1, FADS2, HMGCR, PGC1α, PEPCK, G6Pase, or TNF gene as the target gene for AMPK signaling in order to quantify an expression level of the target gene. The expression level of the quantified gene was expressed as a relative expression level with respect to the expression level of the gene in the MKRN1$^{+/+}$ (WT) fatty liver mouse group.

As a result, as shown in FIG. 13, it was confirmed that the gene expression levels of SREBP1c and chREBP, which are lipogenesis-related regulatory factors known to be inhibited by AMPK activity in hepatocytes, in the MKRN1$^{-/-}$ (KO) fatty liver mouse group, were reduced, and the gene expression levels of PGC1 alpha, PEPCK and G6Pase, which are materials for regulating glucose metabolism inhibited by AMPK activity, were also significantly reduced (FIG. 13). From these results, it was confirmed that MKRN1 KO induced the activity of AMPK to inhibit lipogenesis and suppress development of diabetes and fatty liver.

<5-3> Confirmation of Adenoviral-Mediated Induction of Fatty Liver with Suppression of MKRN1 Expression in Hepatic Tissues in High-Fat Diet Mouse Model The metabolic consequences of chronic AMPK activation exhibited by MKRN1-null mice led us to investigate whether hepatic AMPK activation was sufficient to improve NAFLD without affecting the activation of AMPK in adipose tissue and whether the acute reduction of MKRN1 expression would alleviate the symptoms of hepatic steatosis in obese mice. We generated adenoviruses expressing two independent shRNAs targeting MKRN1 (Ad-shMKRN1#1 and #2) and injected these viruses into diet-induced obese mice via the tail vein to answer these questions (a). Following the delivery of the adenovirus into mice, which was confirmed by GFP co-expression, the adenovirus was predominantly observed in the liver (b). The administration of both Ad-shMKRN1#1 and #2 successfully ablated MKRN1 expression and led to the activation of hepatic AMPK and ACC phosphorylation (c). No apparent changes in BAT were observed (d). Notably, while there was no effect on the body weight of the mice, hepatic MKRN1 knockdown in obese mice dramatically reversed the generation of enlarged lipid droplets and reduced triglyceride levels in the liver (e-g). In addition, the alleviation of hepatic steatosis accompanied the salutary effects on hyperlipidaemia in Ad-shMKRN1-injected obese mice (k). The decreases in SREBP-1 and ChREBP support the reduction of lipid droplets and hypolipidaemia observed in the liver upon MKRN1 knockdown (h). On the other hand, the knockdown of MKRN1 in the liver had no apparent effect on adipose tissues (i, j). These observations reveal that MKRN1 could be a potential therapeutic target for alleviating the symptoms of hepatic steatosis.

Therefore, the present invention provides a pharmaceutical composition for preventing and treating metabolic diseases, which includes an MKRN1 expression or activity inhibitor as an active ingredient.

Because the MKRN1 of the present invention functions as an E3 ligase, which ubiquitinates AMPKα, to degrade an AMPK protein, expression and activity levels of AMPK can be restored by suppressing the MKRN1 expression. Also, the MKRN1 expression or activity inhibitor of the present invention can be effectively used as an active ingredient of the composition for preventing and treating metabolic diseases because an improving effect on obesity, diabetes, and fatty liver can be exhibited by MKRN1 expression knockout in a mouse model in which the MKRN1 expression is knocked out and the obesity, diabetes and fatty liver are induced by high-fat diets.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of treating metabolic diseases, comprising:
administering an effective amount of an MKRN1 expression or activity inhibitor to a subject suffering from a metabolic disease,
wherein the MKRN1 expression or activity inhibitor comprises a siRNA which complementarily binds to mRNA of a gene encoding MKRN1,
wherein the siRNA has the nucleotide sequence of SEQ ID NO: 1 or 2.

2. The method of claim 1, wherein the MKRN1 expression or activity inhibitor enhances the expression and activity of AMPK.

3. The method of claim 1, wherein the metabolic diseases are selected from the group consisting of obesity, type 2 diabetes, dyslipidemia, insulin resistance, hepatic steatosis, and non-alcoholic fatty liver.

* * * * *